(12) United States Patent
Yun et al.

(10) Patent No.: US 10,295,486 B2
(45) Date of Patent: May 21, 2019

(54) DETECTOR FOR X-RAYS WITH HIGH SPATIAL AND HIGH SPECTRAL RESOLUTION

(71) Applicant: SIGRAY, INC., Concord, CA (US)

(72) Inventors: Wenbing Yun, Walnut Creek, CA (US); Sylvia Jia Yun Lewis, San Francisco, CA (US); Janos Kirz, Berkeley, CA (US); Benjamin Donald Stripe, Walnut Creek, CA (US)

(73) Assignee: Sigray, Inc., Concord, CA (US)

( * ) Notice: Subject to any disclaimer, the term of this patent is extended or adjusted under 35 U.S.C. 154(b) by 189 days.

(21) Appl. No.: 15/240,972

(22) Filed: Aug. 18, 2016

(65) Prior Publication Data

US 2017/0052128 A1 Feb. 23, 2017

Related U.S. Application Data

(60) Provisional application No. 62/206,839, filed on Aug. 18, 2015.

(51) Int. Cl.
*G01N 23/223* (2006.01)
*G01N 23/20058* (2018.01)
*G01N 23/04* (2018.01)

(52) U.S. Cl.
CPC .......... *G01N 23/223* (2013.01); *G01N 23/04* (2013.01); *G01N 23/20058* (2013.01);
(Continued)

(58) Field of Classification Search
None
See application file for complete search history.

(56) References Cited

U.S. PATENT DOCUMENTS

| 1,203,495 A | 10/1916 | Coolidge |
| 1,211,092 A | 1/1917 | Coolidge |

(Continued)

FOREIGN PATENT DOCUMENTS

| CN | 102124537 A | 7/2011 |
| EP | 0432568 | 6/1991 |

(Continued)

OTHER PUBLICATIONS

"Diamond," Section 10.4.2 of Zorman et al., "Material Aspects of Micro-Nanoelectromechanical Systems," Chapter 10 of Springer Handbook of Nanotechnology, 2nd ed., Barat Bushan, ed. (Springer Science + Business Media, Inc., New York, 2007), pp. 312-314.

(Continued)

*Primary Examiner* — Hoon K Song
(74) *Attorney, Agent, or Firm* — Knobbe, Martens, Olson & Bear, LLP

(57) ABSTRACT

An x-ray spectrometer system comprising an x-ray imaging system with at least one achromatic imaging x-ray optic and an x-ray detection system. The optical train of the imaging system is arranged so that its object focal plane partially overlaps an x-ray emitting volume of an object. An image of a portion of the object is formed with a predetermined image magnification at the x-ray detection system. The x-ray detection system has both high spatial and spectral resolution, and converts the detected x-rays to electronic signals. In some embodiments, the detector system may have a small aperture placed in the image plane, and use a silicon drift detector to collect x-rays passing through the aperture. In other embodiments, the detector system has an energy resolving pixel array x-ray detector. In other embodiments, wavelength dispersive elements may be used in either the optical train or the detector system.

19 Claims, 13 Drawing Sheets

(52) U.S. Cl.
CPC . *G01N 2223/052* (2013.01); *G01N 2223/056* (2013.01); *G01N 2223/076* (2013.01)

(56) References Cited

U.S. PATENT DOCUMENTS

| | | | |
|---|---|---|---|
| 1,215,116 A | 2/1917 | Coolidge |
| 1,328,495 A | 1/1920 | Coolidge |
| 1,355,126 A | 10/1920 | Coolidge |
| 1,790,073 A | 1/1931 | Pohl |
| 1,917,099 A | 7/1933 | Coolidge |
| 1,946,312 A | 2/1934 | Coolidge |
| 2,926,270 A | 2/1960 | Zunick |
| 3,795,832 A | 3/1974 | Holland |
| 4,227,112 A | 10/1980 | Waugh et al. |
| 4,266,138 A | 5/1981 | Nelson et al. |
| 4,426,718 A | 1/1984 | Hayashi |
| 4,523,327 A | 6/1985 | Eversole |
| 4,573,186 A | 2/1986 | Reinhold |
| 4,807,268 A | 2/1989 | Wittrey |
| 4,940,319 A | 7/1990 | Ueda et al. |
| 4,951,304 A | 8/1990 | Piestrup et al. |
| 4,972,449 A | 11/1990 | Upadhya et al. |
| 5,001,737 A | 3/1991 | Lewis et al. |
| 5,008,918 A | 4/1991 | Lee et al. |
| 5,132,997 A | 7/1992 | Kojima |
| 5,148,462 A | 9/1992 | Spitsyn et al. |
| 5,173,928 A | 12/1992 | Momose et al. |
| 5,249,216 A | 9/1993 | Ohsugi et al. |
| 5,276,724 A | 1/1994 | Kumasaka et al. |
| 5,602,899 A | 2/1997 | Larson |
| 5,604,782 A | 2/1997 | Cash, Jr. |
| 5,629,969 A | 5/1997 | Koshishiba |
| 5,657,365 A | 8/1997 | Yamamoto et al. |
| 5,682,415 A | 10/1997 | O'Hara |
| 5,715,291 A | 2/1998 | Momose |
| 5,729,583 A | 3/1998 | Tang et al. |
| 5,768,339 A | 6/1998 | O'Hara |
| 5,772,903 A | 6/1998 | Hirsch |
| 5,778,039 A | 7/1998 | Hossain |
| 5,812,629 A | 9/1998 | Clauser |
| 5,825,848 A | 10/1998 | Virshup et al. |
| 5,832,052 A | 11/1998 | Hirose et al. |
| 5,857,008 A | 1/1999 | Reinhold |
| 5,878,110 A | 3/1999 | Yamamoto et al. |
| 5,881,126 A | 3/1999 | Momose |
| 5,912,940 A | 6/1999 | O'Hara |
| 5,930,325 A | 7/1999 | Momose |
| 6,108,397 A | 8/2000 | Cash, Jr. |
| 6,108,398 A | 8/2000 | Mazor et al. |
| 6,125,167 A | 9/2000 | Morgan |
| 6,278,764 B1 | 8/2001 | Barbee, Jr. et al. |
| 6,359,964 B1 | 3/2002 | Kogan |
| 6,377,660 B1 | 4/2002 | Ukita et al. |
| 6,381,303 B1 | 4/2002 | Vu et al. |
| 6,389,100 B1 | 5/2002 | Verman et al. |
| 6,430,254 B2 | 8/2002 | Wilkins |
| 6,442,231 B1* | 8/2002 | O'Hara ............ G01N 23/20025 378/145 |
| 6,456,688 B1 | 9/2002 | Taguchi et al. |
| 6,463,123 B1 | 10/2002 | Korenev |
| 6,487,272 B1 | 11/2002 | Kutsuzawa |
| 6,504,902 B2 | 1/2003 | Iwasaki et al. |
| 6,507,388 B2 | 1/2003 | Burghoorn |
| 6,553,096 B1 | 4/2003 | Zhou et al. |
| 6,560,313 B1 | 5/2003 | Harding et al. |
| 6,560,315 B1 | 5/2003 | Price et al. |
| 6,707,883 B1 | 3/2004 | Tiearney et al. |
| 6,711,234 B1 | 3/2004 | Loxley et al. |
| 6,811,612 B2 | 11/2004 | Gruen et al. |
| 6,815,363 B2 | 11/2004 | Yun et al. |
| 6,829,327 B1 | 12/2004 | Chen |
| 6,847,699 B2 | 1/2005 | Rigali et al. |
| 6,850,598 B1 | 2/2005 | Fryda et al. |
| 6,870,172 B1 | 3/2005 | Mankos et al. |
| 6,885,503 B2 | 4/2005 | Yun et al. |
| 6,914,723 B2 | 7/2005 | Yun et al. |
| 6,917,472 B1 | 7/2005 | Yun et al. |
| 6,947,522 B2 | 9/2005 | Wilson et al. |
| 6,975,703 B2 | 12/2005 | Wilson et al. |
| 7,003,077 B2 | 2/2006 | Jen et al. |
| 7,006,596 B1* | 2/2006 | Janik ............ G01N 23/2252 250/310 |
| 7,015,467 B2 | 3/2006 | Maldonado et al. |
| 7,023,955 B2 | 4/2006 | Chen et al. |
| 7,057,187 B1 | 6/2006 | Yun et al. |
| 7,079,625 B2 | 7/2006 | Lenz |
| 7,095,822 B1 | 8/2006 | Yun |
| 7,110,503 B1 | 9/2006 | Kumakhov |
| 7,119,953 B2 | 10/2006 | Yun et al. |
| 7,130,375 B1 | 10/2006 | Yun et al. |
| 7,170,969 B1* | 1/2007 | Yun ............ G21K 1/06 378/43 |
| 7,180,979 B2 | 2/2007 | Momose |
| 7,180,981 B2 | 2/2007 | Wang |
| 7,183,547 B2* | 2/2007 | Yun ............ B82Y 10/00 250/310 |
| 7,215,736 B1 | 5/2007 | Wang et al. |
| 7,215,741 B2 | 5/2007 | Ukita et al. |
| 7,218,700 B2 | 5/2007 | Huber et al. |
| 7,218,703 B2 | 5/2007 | Yada et al. |
| 7,221,731 B2 | 5/2007 | Yada et al. |
| 7,245,696 B2 | 7/2007 | Yun et al. |
| 7,268,945 B2 | 9/2007 | Yun et al. |
| 7,286,640 B2 | 10/2007 | Yun et al. |
| 7,297,959 B2 | 11/2007 | Yun et al. |
| 7,298,826 B2 | 11/2007 | Inazuru |
| 7,330,533 B2 | 2/2008 | Sampayon |
| 7,346,148 B2 | 3/2008 | Ukita |
| 7,346,204 B2 | 3/2008 | Ito |
| 7,359,487 B1 | 4/2008 | Newcome |
| 7,365,909 B2 | 4/2008 | Yun et al. |
| 7,365,918 B1 | 4/2008 | Yun et al. |
| 7,382,864 B2 | 6/2008 | Hebert et al. |
| 7,388,942 B2 | 6/2008 | Wang et al. |
| 7,394,890 B1 | 7/2008 | Wang et al. |
| 7,400,704 B1 | 7/2008 | Yun et al. |
| 7,406,151 B1 | 7/2008 | Yun |
| 7,412,024 B1 | 8/2008 | Yun et al. |
| 7,412,030 B1 | 8/2008 | O'Hara |
| 7,412,131 B2 | 8/2008 | Lee et al. |
| 7,414,787 B2 | 8/2008 | Yun et al. |
| 7,433,444 B2 | 10/2008 | Baumann |
| 7,443,953 B1 | 10/2008 | Yun et al. |
| 7,453,981 B2 | 11/2008 | Baumann |
| 7,463,712 B2 | 12/2008 | Zhu et al. |
| 7,486,770 B2 | 2/2009 | Baumann |
| 7,492,871 B2 | 2/2009 | Popescu |
| 7,499,521 B2 | 3/2009 | Wang et al. |
| 7,515,684 B2 | 4/2009 | Gibson et al. |
| 7,522,698 B2 | 4/2009 | Popescu |
| 7,522,707 B2 | 4/2009 | Steinlage et al. |
| 7,522,708 B2 | 4/2009 | Heismann |
| 7,529,343 B2 | 5/2009 | Safai et al. |
| 7,532,704 B2 | 5/2009 | Hempel |
| 7,551,719 B2 | 6/2009 | Yokhin et al. |
| 7,551,722 B2 | 6/2009 | Ohshima et al. |
| 7,561,662 B2 | 7/2009 | Wang et al. |
| 7,564,941 B2 | 7/2009 | Baumann |
| 7,583,789 B1 | 9/2009 | Macdonald et al. |
| 7,601,399 B2 | 10/2009 | Barnola et al. |
| 7,639,786 B2 | 12/2009 | Baumann |
| 7,646,843 B2 | 1/2010 | Popescu et al. |
| 7,672,433 B2 | 3/2010 | Zhong et al. |
| 7,680,243 B2 | 3/2010 | Yokhin et al. |
| 7,787,588 B1 | 8/2010 | Yun et al. |
| 7,796,725 B1 | 9/2010 | Yun et al. |
| 7,796,726 B1 | 9/2010 | Gendreau et al. |
| 7,800,072 B2 | 9/2010 | Yun et al. |
| 7,813,475 B1 | 10/2010 | Wu et al. |
| 7,817,777 B2 | 10/2010 | Baumann et al. |
| 7,864,426 B2 | 1/2011 | Yun et al. |
| 7,864,922 B2 | 1/2011 | Kawabe |
| 7,873,146 B2 | 1/2011 | Okunuki et al. |
| 7,876,883 B2 | 1/2011 | O'Hara |

(56) References Cited

U.S. PATENT DOCUMENTS

| | | |
|---|---|---|
| 7,889,838 B2 | 2/2011 | David et al. |
| 7,889,844 B2 | 2/2011 | Okunuki et al. |
| 7,914,693 B2 | 3/2011 | Jeong et al. |
| 7,920,673 B2 | 4/2011 | Lanza et al. |
| 7,920,676 B2 | 4/2011 | Yun et al. |
| 7,924,973 B2 | 4/2011 | Kottler et al. |
| 7,929,667 B1 | 4/2011 | Zhuang et al. |
| 7,945,018 B2 | 5/2011 | Heismann |
| 7,949,092 B2 | 5/2011 | Brons |
| 7,949,095 B2 | 5/2011 | Ning |
| 7,974,379 B1 | 7/2011 | Case et al. |
| 7,983,381 B2 | 7/2011 | David et al. |
| 7,991,120 B2 | 8/2011 | Okunuki et al. |
| 8,005,185 B2 | 8/2011 | Popescu |
| 8,009,796 B2 | 8/2011 | Popescu |
| 8,041,004 B2 | 10/2011 | David |
| 8,036,341 B2 | 11/2011 | Lee |
| 8,058,621 B2 | 11/2011 | Kommareddy |
| 8,068,579 B1 | 11/2011 | Yun et al. |
| 8,073,099 B2 | 12/2011 | Niu et al. |
| 8,094,784 B2 | 1/2012 | Morton |
| 8,139,716 B2 | 3/2012 | Okunuki et al. |
| 8,184,771 B2 | 5/2012 | Murakoshi |
| 8,208,602 B2 | 6/2012 | Lee |
| 8,208,603 B2 | 6/2012 | Sato |
| 8,243,879 B2 | 8/2012 | Itoh et al. |
| 8,243,884 B2 | 8/2012 | Rödhammer et al. |
| 8,280,000 B2 | 10/2012 | Takahashi |
| 8,306,183 B2 | 11/2012 | Koehler |
| 8,306,184 B2 | 11/2012 | Chang et al. |
| 8,351,569 B2 | 1/2013 | Baker |
| 8,351,570 B2 | 1/2013 | Nakamura |
| 8,353,628 B1 | 1/2013 | Yun et al. |
| 8,360,640 B2 | 1/2013 | Reinhold |
| 8,374,309 B2 | 2/2013 | Donath |
| 8,406,378 B2 | 3/2013 | Wang et al. |
| 8,416,920 B2 | 4/2013 | Okumura et al. |
| 8,422,633 B2 | 4/2013 | Lantz et al. |
| 8,451,975 B2 | 5/2013 | Tada |
| 8,422,637 B2 | 6/2013 | Okunuki et al. |
| 8,509,386 B2 | 8/2013 | Lee et al. |
| 8,520,803 B2 | 8/2013 | Behling |
| 8,526,575 B1 | 9/2013 | Yun et al. |
| 8,532,257 B2 | 9/2013 | Mukaide et al. |
| 8,553,843 B2 | 10/2013 | Drory |
| 8,559,597 B2 | 10/2013 | Chen et al. |
| 8,565,371 B2 | 10/2013 | Bredno |
| 8,576,983 B2 | 11/2013 | Baeumer |
| 8,591,108 B2 | 11/2013 | Tada |
| 8,602,648 B1 | 12/2013 | Jacobsen et al. |
| 8,632,247 B2 | 1/2014 | Ishii |
| 8,666,024 B2 | 3/2014 | Okunuki et al. |
| 8,666,025 B2 | 3/2014 | Klausz |
| 8,699,667 B2 | 4/2014 | Steinlage et al. |
| 8,735,844 B1 | 5/2014 | Khaykovich et al. |
| 8,737,565 B1 | 5/2014 | Lyon et al. |
| 8,744,048 B2 | 6/2014 | Lee et al. |
| 8,755,487 B2 | 6/2014 | Kaneko |
| 8,767,915 B2 | 7/2014 | Stutman |
| 8,767,916 B2 | 7/2014 | Hashimoto |
| 8,781,069 B2 | 7/2014 | Murakoshi |
| 8,824,629 B2 | 9/2014 | Ishii |
| 8,831,174 B2 | 9/2014 | Kohara |
| 8,831,175 B2 | 9/2014 | Silver et al. |
| 8,831,179 B2 | 9/2014 | Adler et al. |
| 8,855,265 B2 | 10/2014 | Engel |
| 8,861,682 B2 | 10/2014 | Okunuki et al. |
| 8,903,042 B2 | 12/2014 | Ishii |
| 8,995,622 B2 | 3/2015 | Adler et al. |
| 9,001,967 B2 | 4/2015 | Baturin |
| 9,008,278 B2 | 4/2015 | Lee et al. |
| 9,016,943 B2 | 4/2015 | Jacobsen et al. |
| 9,020,101 B2 | 4/2015 | Omote et al. |
| 9,129,715 B2 | 9/2015 | Adler et al. |
| 9,329,141 B2 | 5/2016 | Stutman |
| 9,357,975 B2 | 6/2016 | Baturin |
| 9,390,881 B2 | 7/2016 | Yun et al. |
| 9,439,613 B2 | 9/2016 | Stutman |
| 9,448,190 B2 | 9/2016 | Yun et al. |
| 9,449,781 B2 | 9/2016 | Yun et al. |
| 9,543,109 B2 | 1/2017 | Yun et al. |
| 9,570,265 B1 | 2/2017 | Yun et al. |
| 9,594,036 B2 | 3/2017 | Yun et al. |
| 9,632,040 B2 | 4/2017 | Stutman |
| 9,719,947 B2 | 8/2017 | Yun et al. |
| 9,823,203 B2 | 11/2017 | Yun et al. |
| 9,874,531 B2 | 1/2018 | Yun et al. |
| 9,939,392 B2 | 4/2018 | Wen |
| 10,151,713 B2 | 12/2018 | Wu et al. |
| 10,153,062 B2 | 12/2018 | Gall et al. |
| 2001/0006413 A1 | 7/2001 | Burghoorn |
| 2002/0085676 A1 | 7/2002 | Snyder |
| 2003/0142790 A1 | 1/2003 | Zhou et al. |
| 2003/0223536 A1* | 12/2003 | Yun ........... B82Y 10/00 378/45 |
| 2004/0047446 A1* | 3/2004 | Platonov ........ B82Y 10/00 378/42 |
| 2004/0120463 A1 | 6/2004 | Wilson et al. |
| 2004/0140432 A1 | 7/2004 | Maldonado et al. |
| 2005/0074094 A1 | 4/2005 | Jen et al. |
| 2005/0123097 A1 | 6/2005 | Wang |
| 2005/0163284 A1 | 7/2005 | Inazuru |
| 2005/0282300 A1 | 12/2005 | Yun et al. |
| 2006/0045234 A1 | 3/2006 | Pelc |
| 2006/0062350 A1 | 3/2006 | Yokhin |
| 2007/0030959 A1 | 2/2007 | Ritter |
| 2007/0071174 A1 | 3/2007 | Hebert et al. |
| 2007/0103387 A1 | 5/2007 | Yun et al. |
| 2007/0110217 A1 | 5/2007 | Ukita |
| 2007/0183563 A1 | 8/2007 | Baumann |
| 2007/0183579 A1 | 8/2007 | Baumann et al. |
| 2007/0189449 A1 | 8/2007 | Baumann |
| 2007/0248215 A1 | 10/2007 | Ohshima et al. |
| 2008/0084966 A1 | 4/2008 | Aoki et al. |
| 2008/0089484 A1 | 4/2008 | Reinhold |
| 2008/0094694 A1 | 4/2008 | Yun et al. |
| 2008/0159707 A1 | 7/2008 | Lee et al. |
| 2008/0165355 A1 | 7/2008 | Yasui et al. |
| 2008/0170662 A1 | 7/2008 | Reinhold |
| 2008/0170668 A1 | 7/2008 | Kruit et al. |
| 2008/0181363 A1 | 7/2008 | Fenter et al. |
| 2008/0240344 A1 | 10/2008 | Reinhold |
| 2008/0273662 A1 | 11/2008 | Yun |
| 2009/0052619 A1 | 2/2009 | Endoh |
| 2009/0092227 A1 | 4/2009 | David |
| 2009/0154640 A1 | 6/2009 | Baumann et al. |
| 2009/0316860 A1 | 12/2009 | Okunuki et al. |
| 2010/0012845 A1 | 1/2010 | Baeumer et al. |
| 2010/0027739 A1 | 2/2010 | Lantz et al. |
| 2010/0040202 A1 | 2/2010 | Lee |
| 2010/0046702 A1* | 2/2010 | Chen ............ G01N 23/223 378/45 |
| 2010/0061508 A1 | 3/2010 | Takahashi |
| 2010/0091947 A1 | 4/2010 | Niu |
| 2010/0141151 A1 | 6/2010 | Reinhold |
| 2010/0246765 A1 | 9/2010 | Murakoshi |
| 2010/0260315 A1 | 10/2010 | Sato et al. |
| 2010/0272239 A1 | 10/2010 | Lantz et al. |
| 2010/0284513 A1 | 11/2010 | Kawabe |
| 2011/0026680 A1 | 2/2011 | Sato |
| 2011/0038455 A1 | 2/2011 | Silver et al. |
| 2011/0058655 A1 | 3/2011 | Okumura et al. |
| 2011/0064191 A1 | 3/2011 | Toth et al. |
| 2011/0085644 A1 | 4/2011 | Verman |
| 2011/0135066 A1 | 6/2011 | Behling |
| 2011/0142204 A1 | 6/2011 | Zou et al. |
| 2011/0235781 A1 | 9/2011 | Aoki et al. |
| 2011/0243302 A1 | 10/2011 | Murakoshi |
| 2011/0268252 A1 | 11/2011 | Ozawa et al. |
| 2012/0041679 A1 | 2/2012 | Stampanoni |
| 2012/0057669 A1 | 3/2012 | Vogtmeier et al. |
| 2012/0163547 A1 | 6/2012 | Lee et al. |
| 2012/0163554 A1 | 6/2012 | Tada |
| 2012/0224670 A1 | 9/2012 | Kiyohara et al. |

(56) References Cited

U.S. PATENT DOCUMENTS

| | | |
|---|---|---|
| 2012/0228475 A1 | 9/2012 | Pang et al. |
| 2012/0269323 A1 | 10/2012 | Adler et al. |
| 2012/0269324 A1 | 10/2012 | Adler |
| 2012/0269325 A1 | 10/2012 | Adler et al. |
| 2012/0269326 A1 | 10/2012 | Adler et al. |
| 2012/0294420 A1 | 11/2012 | Nagai |
| 2013/0011040 A1 | 1/2013 | Kido et al. |
| 2013/0032727 A1 | 2/2013 | Kondoe |
| 2013/0039460 A1* | 2/2013 | Levy .............. G01N 21/211 378/44 |
| 2013/0108012 A1 | 5/2013 | Sato |
| 2013/0108022 A1 | 5/2013 | Kugland et al. |
| 2013/0195246 A1 | 8/2013 | Tamura et al. |
| 2013/0223594 A1 | 8/2013 | Sprong et al. |
| 2013/0259207 A1 | 10/2013 | Omote et al. |
| 2013/0279651 A1 | 10/2013 | Yokoyama |
| 2013/0308112 A1 | 11/2013 | Clube et al. |
| 2013/0308754 A1 | 11/2013 | Yamazaki et al. |
| 2014/0023973 A1 | 1/2014 | Marconi et al. |
| 2014/0037052 A1 | 2/2014 | Adler |
| 2014/0064445 A1 | 3/2014 | Adler |
| 2014/0072104 A1 | 3/2014 | Jacobsen et al. |
| 2014/0079188 A1 | 3/2014 | Hesselink et al. |
| 2014/0105363 A1 | 4/2014 | Chen et al. |
| 2014/0146945 A1 | 5/2014 | Fredenberg et al. |
| 2014/0153692 A1 | 6/2014 | Larkin et al. |
| 2014/0177800 A1 | 6/2014 | Sato et al. |
| 2014/0185778 A1 | 7/2014 | Lee et al. |
| 2014/0205057 A1 | 7/2014 | Koehler et al. |
| 2014/0211919 A1 | 7/2014 | Ogura et al. |
| 2014/0226785 A1 | 8/2014 | Stutman et al. |
| 2014/0241493 A1 | 8/2014 | Yokoyama |
| 2014/0270060 A1 | 9/2014 | Date et al. |
| 2014/0369469 A1 | 12/2014 | Ogura et al. |
| 2015/0030126 A1 | 1/2015 | Radicke |
| 2015/0030127 A1 | 1/2015 | Aoki et al. |
| 2015/0043713 A1 | 2/2015 | Chen |
| 2015/0049860 A1 | 2/2015 | Das |
| 2015/0055743 A1 | 2/2015 | Vedantham et al. |
| 2015/0055745 A1 | 2/2015 | Holzner et al. |
| 2015/0092924 A1 | 4/2015 | Yun et al. |
| 2015/0110252 A1 | 4/2015 | Yun et al. |
| 2015/0117599 A1 | 4/2015 | Yun et al. |
| 2015/0194287 A1 | 7/2015 | Yun et al. |
| 2015/0243397 A1 | 8/2015 | Yun et al. |
| 2015/0247811 A1 | 9/2015 | Yun et al. |
| 2015/0260663 A1 | 9/2015 | Yun et al. |
| 2015/0357069 A1 | 12/2015 | Yun et al. |
| 2016/0064175 A1 | 3/2016 | Yun et al. |
| 2016/0066870 A1 | 3/2016 | Yun et al. |
| 2016/0106387 A1 | 4/2016 | Kahn |
| 2016/0178540 A1 | 6/2016 | Yun et al. |
| 2016/0268094 A1 | 9/2016 | Yun et al. |
| 2016/0320320 A1 | 11/2016 | Yun et al. |
| 2016/0351370 A1 | 12/2016 | Yun et al. |
| 2017/0047191 A1 | 2/2017 | Yun et al. |
| 2017/0052128 A1 | 2/2017 | Yun et al. |
| 2017/0162288 A1 | 6/2017 | Yun et al. |
| 2017/0162359 A1 | 6/2017 | Tang et al. |
| 2017/0227476 A1 | 8/2017 | Zhang et al. |
| 2017/0234811 A1 | 8/2017 | Zhang et al. |
| 2017/0261442 A1 | 9/2017 | Yun et al. |
| 2017/0336334 A1 | 11/2017 | Yun et al. |
| 2018/0144901 A1 | 5/2018 | Yun et al. |
| 2018/0261352 A1 | 9/2018 | Matsuyama et al. |
| 2018/0306734 A1 | 10/2018 | Morimoto et al. |
| 2018/0323032 A1 | 11/2018 | Strelec et al. |
| 2018/0344276 A1 | 12/2018 | DeFreitas et al. |
| 2018/0348151 A1 | 12/2018 | Kasper et al. |
| 2018/0356355 A1 | 12/2018 | Momose et al. |

FOREIGN PATENT DOCUMENTS

| | | |
|---|---|---|
| EP | 0751533 | 1/1997 |
| EP | 1028451 | 8/2000 |
| FR | 2548447 | 1/1985 |
| JP | H06-188092 | 7/1994 |
| JP | H07-056000 | 3/1995 |
| JP | H08-184572 | 7/1996 |
| JP | 2000-306533 | 11/2000 |
| JP | 2003-288853 | 10/2003 |
| JP | 2004-089445 | 3/2004 |
| JP | 2007-218683 | 8/2007 |
| JP | 2007-265981 | 10/2007 |
| JP | 2007-311185 | 11/2007 |
| JP | 2008-200359 | 4/2008 |
| JP | 2008-145111 | 6/2008 |
| JP | 2008-197495 | 8/2008 |
| JP | 2009-195349 | 3/2009 |
| JP | 2009-212058 | 9/2009 |
| JP | 2010-236986 | 10/2010 |
| JP | 2011-029072 | 2/2011 |
| JP | 2011-218147 | 11/2011 |
| JP | 2012-032387 | 2/2012 |
| JP | 2012-187341 | 10/2012 |
| JP | 2012-254294 | 12/2012 |
| JP | 2013-508683 | 3/2013 |
| JP | 2013-157269 | 8/2013 |
| JP | 2013-160637 | 8/2013 |
| JP | 2013-239317 | 11/2013 |
| JP | 2015-002074 | 1/2015 |
| JP | 2015-047306 | 3/2015 |
| JP | 2015-077289 | 4/2015 |
| WO | WO 1995/006952 | 3/1995 |
| WO | WO 1998/011592 | 3/1998 |
| WO | WO 2002/039792 | 5/2002 |
| WO | WO 2003/081631 | 10/2003 |
| WO | WO 2005/109969 | 11/2005 |
| WO | WO 2006/096052 | 9/2006 |
| WO | WO 2007/125833 | 11/2007 |
| WO | WO 2009/098027 | 8/2009 |
| WO | WO 2009/104560 | 8/2009 |
| WO | WO 2011/032572 | 3/2011 |
| WO | WO 2012/032950 | 3/2012 |
| WO | WO 2013/004574 | 1/2013 |
| WO | WO 2013/111050 | 8/2013 |
| WO | WO 2013/118593 | 8/2013 |
| WO | WO 2013/160153 | 10/2013 |
| WO | WO 2013/168468 | 11/2013 |
| WO | WO 2014/054497 | 4/2014 |
| WO | WO 2015/016019 | 2/2015 |
| WO | WO 2015/034791 | 3/2015 |
| WO | WO 2015/066333 | 5/2015 |
| WO | WO 2015/084466 | 6/2015 |
| WO | WO 2015/168473 | 11/2015 |
| WO | WO 2015/176023 | 11/2015 |
| WO | WO 2015/187219 | 12/2015 |
| WO | WO 2016/187623 | 11/2016 |
| WO | WO 2017/031740 | 3/2017 |
| WO | WO 2017/204850 | 11/2017 |
| WO | WO 2017/213996 | 12/2017 |
| WO | WO 2018/175570 | 9/2018 |

OTHER PUBLICATIONS

"Element Six CVD Diamond Handbook" (Element Six, Luxembourg, 2015).
"High performance benchtop EDXRF spectrometer with Windows® software," published by: Rigaku Corp., Tokyo, Japan; 2017.
"Monochromatic Doubly Curved Crystal Optics," published by: X-Ray Optical Systems, Inc. (XOS), East Greenbush, NY; 2017.
"Optics and Detectors," Section 4 of XS-Ray Data Booklet, 3rd Ed., A.C. Thompson ed. (Lawrence Berkeley Nat'l Lab, Berkeley, CA, 2009).
"Properties of Solids," Ch. 12 of CRC Handbook of Chemistry and Physics, 90th ed., Devid R. Lide & W.M. "Mickey" Haynes, eds. (CRC Press, Boca Raton, FL, 2009), pp. 12-41-12-46; 12-203-12-212.

(56) References Cited

OTHER PUBLICATIONS

"Science and Technology of Future Light Sources", Arthur L. Robinson (LBNL) and Brad Plummer (SLAG), eds. Report Nos. ANL-08/39 / BNL-81895-2008 / LBNL-1090E-2009 / SLAC-R-917 (Lawrence Berkeley Nal'l Lab, Berkeley, CA, Dec. 2008).
"Series 5000 Packaged X-ray Tubes," Product Technical Data Sheet DS006 Rev. G, X-Ray Technologies Inc. (Oxford Insstruments), Scotts Valley, CA (no date).
"Toward Control of Matter: Energy Science Needs for a New Class of X-Ray Light Sources" (Lawrence Berkeley Nal'l Lab, Berkeley, CA, Sep. 2008).
"X-ray Optics for BES Light Source Facilities," Report of the Basic Energy Sciences Workshop on X-ray Optics for BES Light Source Facilities, D. Mills & H. Padmore, Co-Chairs, (U.S. Dept. of Energy, Office of Science, Potomac, MD, Mar. 2013).
Abullian et al., "Quantitative determination of the lateral density and intermolecular correlation between proteins anchored on the membrane surfaces using grazing incidence small-angle X-ray scattering and grazing incidence X-ray fluorescence," Nov. 28, 2012, The Journal of Chemical Physics, vol. 137, pp. 204907-1 to 204907-8.
Adachi et al., "Development of the 17-inch Direct-Conversion Dynamic Flat-panel X-ray Detector (FPD)," Digital R/F (Shimadzu Corp., 2 pages (no date, published—2004 with product release).
Aharonovich et al., "Diamond Nanophotonics," Adv. Op. Mat'ls vol. 2, Issue 10 (2014).
Als-Nielsen et al., "Phase contrast imaging" Sect. 9.3 of Ch. 9 of "Elements of Modern X-ray Physics, Second Edition", (John Wiley & Sons Ltd, Chichester, West Sussex, UK, 2011), pp. 318-329.
Als-Nielsen et al., "Photoelectric Absorption," Ch. 7 of "Elements of Modern X-ray Physics, Second Edition," (John Wiley & Sons Ltd, Chichester, West Sussex, UK, 2011).
Als-Nielsen et al., "Refraction and reflection from interfaces," Ch. 3 of "Elements of Modern X-ray Physics, Second Edition," (John Wiley & Sons Ltd., Chichester, West Sussex, UK, 2011), pp. 69-112.
Als-Nielsen et al., "X-rays and their interaction with matter", and "Sources", Ch. 1 & 2 of "Elements of Modern X-ray Physics, Second Edition" (John Wiley & Sons Ltd, Chichester, West Sussex, UK, 2011).
Altapova et al., "Phase contrast laminography based on Talbot interferometry," Opt. Express, vol. 20, No. 6, (2012) pp. 6496-6508.
Ando et al., "Smooth and high-rate reactive ion etching of diamond," Diamond and Related Materials, vol. 11, (2002) pp. 824-827.
Arfelli et al., "Mammography with Synchrotron Radiation: Phase-Detection Techniques," Radiology vol. 215, (2000), pp. 286-293.
Arndt et al., "Focusing Mirrors for Use with Microfocus X-ray Tubes, 1998, Journal of Applied Crystallography, vol. 31, pp. 733-741.
Balaic et al., "X-ray optics of tapered capillaries," Appl. Opt. vol. 34 (Nov. 1995) pp. 7263-7272.
Baltes et al., "Coherent and incoherent grating reconstruction," J. Opt. Soc. Am. A vol. 3(8), (1986), pp. 1268-1275.
Barbee Jr., "Multilayers for x-ray optics," Opt. Eng. vol. 25 (Aug. 1986) pp. 898-915.
Baron et al., "A compact optical design for Bragg reflections near backscattering," J. Synchrotron Rad., vol. 8 (2001), pp. 1127-1130.
Bech, "In-vivo dark-field and phase-contrast x-ray imaging," Scientific Reports 3, (2013), Article No. 03209.
Bech, "X-ray imaging with a grating interferometer," University of Copenhagan PhD. Thesis, (May 1, 2009).
Bergamin et al., "Measuring small lattice distortions in Si-crystals by phase-contrast x-ray topography," J. Phys. D: Appl. Phys. vol. 33 (Dec. 31, 2000) pp. 2678-2682.
Bernstorff, "Grazing Incidence Small Angle X-ray Scattering (GISAXS)," Presentation at Advanced School on Synchrotron and Free Electron Laser Sources and their Multidisciplinary Applications, Apr. 2008, Trieste, Italy.

Bilderback et al., "Single Capillaries," Ch. 29 of "Handbook of Optics vol. III, 2nd Ed." (McGraw Hill, New York, 2001).
Birkholz, "Chapter 4: Grazing Incidence Configurations," Thin Film Analysis by X-ray Scattering (Wiley-VCH Verlag GmbH & Co. KGaA, Weinheim, Germany, 2006).
Bjeoumikhov et al., "A modular system for XRF and XRD applications consisting of a microfocus X-ray source and different capillary optics," X-ray Spectrometry, vol. 33 (2004), pp. 312-316.
Bjeoumikhov et al., "Capillary Optics for X-Rays," Ch. 18 of "Modern Developments in X-Ray and Neutron Optics," A. Erko et al., eds. (Springer, Berlin, Germany, 2008), pp. 287-306.
Canberra Model S-5005 WinAxil X-Ray Analysis Software, published by: Canberra Eurisys Benelux N.V./S.A.,Zellik, Belgium; Jun. 2004.
Cerrina, "The Schwarzschild Objective," Ch. 27 of "Handbook of Optics vol. III, 2nd Ed." (McGraw Hill, New York, 2001).
Chen et al., "Advance in detection of low sulfur content by wavelength dispersive XRF," Proceedings of the Annual ISA Analysis Division Symposium (2002).
Chen et al., "Doubly curved crystal (DCC) X-ray optics and applications," Powder Diffraction, vol. 17(2) (2002), pp. 99-103.
Chen et al., "Guiding and focusing neutron beams using capillary optics," Nature vol. 357 (Jun. 4, 1992), pp. 391-393.
Chervenak et al., "Experimental thick-target bremsstrahlung spectra from electrons in the range 10 to 30 keV", Phys. Rev. A vol. 12 (1975), pp. 26-33.
Coan et al., "In vivo x-ray phase contrast analyzer-based imaging for longitudinal osteoarthritis studies in guinea pigs," Phys. Med. Biol. vol. 55(24) (2010), pp. 7649-7662.
Cockcroft et al., "Chapter 2: Experimental Setups," Powder Diffraction: Theory and Practice, R.E. Dinnebier and S.J.L. Billinge, eds (Royal Society of Chemistry Publishing, London, UK, 2008).
Cohen et al., "Tunable laboratory extended x-ray absorption fine structure system," Rev. Sci. Instr. vol. 51, No. 3, Mar. 1980, pp. 273-277.
Cong et al., "Fourier transform-based iterative method for differential phase-contrast computed tomography", Opt. Lett. vol. 37 (2012), pp. 1784-1786.
Cornaby et al., "Advances in X-ray Microfocusing with Monocapillary Optics at CHESS," CHESS News Magazine (2009), pp. 63-66.
Cornaby et al., "Design of Single-Bounce Monocapillary X-ray Optics," Advances in X-ray Analysis: Proceedings of the 55th Annual Conference on Applications of X-ray Analysis, vol. 50, (International Centre for Diffraction Data (ICDD), 2007), pp. 194-200.
Cornaby, "The Handbook of X-ray Single Bounce Monocapillary Optics, Including Optical Design and Synchrotron Applications" (PhD Dissertation, Cornell University, Ithaca, NY, May 2008).
David et al., "Fabrication of diffraction gratings for hard x-ray phase contrast imaging," Microelectron. Eng. vol. 84, (2007), pp. 1172-1177.
David et al., "Hard X-ray phase imaging and tomography using a grating interferometer," Spectrochimica Acta Part B vol. 62 (2007) pp. 626-630.
Davis et al., "Bridging the Micro-to-Macro Gap: A New Application for Micro X-Ray Fluorescence," Microsc Microanal., vol. 17(3) (Jun. 2011), pp. 410-417.
Diaz et al., "Monte Carlo Simulation of Scatter Field for Calculation of Contrast of Discs in Synthetic CDMAM Images," In: Digital Mammography, Proceedings 10th International Workshop IWDM 2010 (Springer Verlag, Berlin Heidelberg), (2010), pp. 628- 635 (9 pages). Jun. 18, 2010.
Ding et al., "Reactive Ion Etching of CVD Diamond Films for MEMS Applications," Micromachining and Microfabrication, Proc. SPIE vol. 4230 (2000), pp. 224-230.
Dobrovinskaya et al., "Thermal Properties," Sect. 2.1.5 of "Sapphire: Material, Manufacturing,, Applications" (Springer Science + Business Media, New York, 2009).
Dong et al., "Improving Molecular Sensitivity in X-Ray Fluorescence Molecular Imaging (XFMI) of Iodine Distribution in Mouse-Sized Phantoms via Excitation Spectrum Optimization," IEEE Access, vol. 6, pp. 56966-56976 (2018).

(56) References Cited

OTHER PUBLICATIONS

Erko et al., "X-ray Optics," Ch. 3 of "Handbook of Practical X-Ray Fluorescence Analysis," B. Beckhoff et al., eds. (Springer, Berlin, Germany, 2006), pp. 85-198.
Falcone et al., "New directions in X-ray microscopy," Contemporary Physics, vol. 52, No. 4, (Jul.-Aug. 2010), pp. 293-318.
Fernández-Ruiz, "TXRF Spectrometry as a Powerful Tool for the Study of Metallic Traces in Biological Systems," Development in Analytical Chemistry, vol. 1 (2014), pp. 1-14.
Freund, "Mirrors for Synchrotron Beamlines," Ch. 26 of "Handbook of Optics vol. III, 2nd Ed." (McGraw Hill, New York, 2001).
Ge et al., "Investigation of the partially coherent effects in a 2D Talbot interferometer," Anal. Bioanal. Chem. vol. 401, (2011), pp. 865-870. Apr. 29, 2011 pub Jun. 14, 2011.
Gibson et al., "Polycapillary Optics: An Enabling Technology for New Applications," Advances in X-ray Analysis, vol. 45 (2002), pp. 286-297.
Gonzales et al., "Angular Distribution of Bremsstrahlung Produced by 10-Kev and 20 Kev Electrons Incident on a Thick Au Target", in Application of Accelerators in Research and Industry, AIP Conf. Proc. 1221 (2013), pp. 114-117.
Gonzales et al., "Angular distribution of thick-target bremsstrahlung produced by electrons with initial energies ranging from 10 to 20 keV incident on Ag", Phys. Rev. A vol. 84 (2011): 052726.
Guttmann et al., "Ellipsoidal capillary as condenser for the Besssy full-field x-ray microscope," J. Phys. Conf. Ser. vol. 186 (2009): 012064.
Harasse et al., "Iterative reconstruction in x-ray computed laminography from differential phase measurements", Opt. Express. vol. 19 (2011), pp. 16560-16573.
Harasse et al., "X-ray Phase Laminography with a Grating Interferometer using Iterative Reconstruction", in International Workshop on X-ray and Neutron Phase Imaging with Gratings, AIP Conf. Proc. vol. 1466, (2012), pp. 163-168.
Harasse et al., "X-ray Phase Laminography with Talbot Interferometer", in Developments in X-Ray Tomography VII, Proc. SPIE vol. 7804 (2010), 780411.
Hasse et al., "New developments in laboratory-based x-ray sources and optics," Adv. In Laboratory-based X-Ray Sources, Optics, and Applications VI, ed. A.M. Khounsary, Proc. SPIE vol. 10387, 103870B-1 (2017).
Hemraj-Benny et al., "Near-Edge X-ray Absorption Fine Structure Spectroscopy as a Tool for Investigating Nanomaterials," Small, vol. 2(1), (2006), pp. 26-35.
Henke et al., "X-ray interactions: photoabsorption, scattering, transmission, and reflection at E=50-30000 eV, Z=1-92," Atomic Data and Nuclear Data Tables, vol. 54 (No. 2) (Jul. 1993), pp. 181-342.
Hennekam et al., "Trace metal analysis of sediment cores using a novel X-ray fluorescence core scanning method," Quaternary Int'l, https://doi.org/10.1016/j.quaint.2018.10.018 (2018).
Honma et al., Full-automatic XAFS Measurement System of the Engineering Science Research II beamline BL14B2 at Spring-8, 2011, AIP Conference Proceedings 1234, pp. 13-16.
Howard et al., "High-Definition X-ray Fluorescence Elemental Mapping of Paintings," Anal. Chem., 2012, vol. 84(7), pp. 3278-3286.
Howells, "Gratings and Monochromators in the VUV and Soft X-RAY Spectral Region," Ch. 21 of Handbook of Optics vol. III, 2nd Ed. (McGraw Hill, New York, 2001).
Howells, "Mirrors for Synchrotron-Radiation Beamlines," Publication LBL-34750 (Lawrence Berkeley Laboratory, Berkeley, CA, Sep. 1993).
Hrdy et al, "Diffractive-Refractive Optics: X-ray Crystal Monochromators with Profiled Diffracting Surfaces," Ch. 20 of "Modern Developments in X-Ray and Neutron Optics," A. Erko et al., eds. (Springer, Berlin Heidelberg New York, 2008).
Hwang et al, "New etching process for device fabrication using diamond," Diamond & Related Materials, vol. 13 (2004) pp. 2207-2210.
Ide-Ektessabi et al., "The role of trace metallic elements in neurodegenerative disorders: quantitative analysis using XRF and XANES spectroscopy," Anal. Sci., vol. 21(7) (Jul. 2005), pp. 885-892.
Ihsan et al., "A microfocus X-ray tube based on a microstructured X-ray target", Nuclear Instruments and Methods in Physics Research B vol. 267 (2009) pp. 3566-3573.
Ishisaka et al., "A New Method of Analyzing Edge Effect in Phase Contrast Imaging with Incoherent X-rays," Optical Review, vol. 7, No. 6, (2000), pp. 566-572.
Ito et al., "A Stable In-Laboratory EXAFS Measurement System," Jap. J. Appl. Phys., vol. 22, No. 2, Feb. 1, 1983, pp. 357-360.
Itoh et al., "Two-dimensional grating-based X-ray phase-contrast imaging using Fourier transform phase retrieval," Op. Express, vol. 19, No. 4 (2011) pp. 3339-3346.
Janssens et al, "Recent trends in quantitative aspects of microscopic X-ray fluorescence analysis," TrAC Trends in Analytical Chemistry 29.6 (Jun. 2010): 464-478.
Jahrman et al., "Vacuum formed temporary spherically and toroidally bent crystal analyzers for x-ray absorption and x-ray emission spectroscopy," Rev. Sci. Inst. vol. 90, 013106 (2019).
Jiang et al., "X-Ray Phase-Contrast Imaging with Three 2D Gratings," Int. J. Biomed. Imaging, (2008), 827152, 8 pages.
Joy, "Astronomical X-ray Optics," Ch. 28 of "Handbook of Optics vol. III, 2nd Ed.," (McGraw Hill, New York, 2001).
Keyrilainen et al., "Phase contrast X-ray imaging of breast," Acta Radiologica, vol. 51 (8), (2010), pp. 866-884. Jan. 18, 2010 pub Jun. 15, 2010.
Kidalov et al., "Thermal Conductivity of Diamond Composites," Materials, vol. 2 (2009) pp. 2467-2495.
Kido et al., "Bone Cartilage Imaging with X-ray Interferometry using a Practical X-ray Tube", in Medical Imaging 2010: Physics of Medical Imaging, Proc. SPIE vol. 7622 (2010), 762240.
Kim, "Talbot images of wavelength-scale amplitude gratings," Opt. Express vol. 20(5), (2012), pp. 4904-4920.
Kirkpatrick et al., "Formation of Optical Images by X-Rays", J. Opt. Soc. Am. vol. 38(9) (1948), pp. 766-774.
Kirz, "Phase zone plates for x rays and the extreme uv," J. Op. Soc. Am. vol. 64 (Mar. 1974), pp. 301-309.
Kirz et al., "The History and Future of X-ray Microscopy", J. Physics: Conden. Series vol. 186 (2009): 012001.
Kiyohara et al., "Development of the Talbot-Lau Interferometry System Available for Clinical Use", in International Workshop on X-ray and Neutron Phase Imaging with Gratings, AIP Cong. Proc. vol. 1466, (2012), pp. 97-102.
Klockenkämper et al., "7.1 Instrumental Developments" and "7.3 Future Prospects by Combinations," from Chapter 7 of Total Reflection X-ray Fluorescence Analysis and Related Methods 2nd Ed. (J. Wiley and Sons, Hoboken, NJ, 2015).
Klockenkämper et al., "Chapter 3: Instrumentation for TXRF and GI-XRF," Total Reflection X-ray Fluorescence Analysis and Related Methods 2nd Ed. (J. Wiley and Sons, Hoboken, NJ, 2015).
Kottler et al., "A two-directional approach for grating based differential phase contrast imaging using hard x-rays," Opt. Express vol. 15(3), (2007), pp. 1175-1181.
Kottler et al., "Dual energy phase contrast x-ray imaging with Talbot-Lau interferometer," J. Appl. Phys. vol. 108(11), (2010), 114906. Jul. 7, 2010 pub Dec. 7, 2010.
Kumakhov et al., "Multiple reflection from surface X-ray optics," Physics Reports, vol. 191(5), (1990), pp. 289-350.
Kumakhov, "X-ray Capillary Optics. History of Development and Present Status" in Kumakhov Optics and Application, Proc. SPIE 4155 (2000), pp. 2-12.
Kuwabara et al., "Hard-X-ray Phase-Difference Microscopy with a Low-Brilliance Laboratory X-ray Source", Appl. Phys. Express vol. 4 (2011) 062502.
Kuznetsov, "X-Ray Optics Calculator," Institute of Microelectronics Technology and High Purity Materials, Russian Academy of Sciences (IMT RAS), Chernogolovka, Russia (6 pages submitted); 2016.
Lagomarsino et al., "Reflective Optical Arrays," Ch. 19 of "Modern Developments in X-Ray and Neutron Optics," A. Erko et al. eds. (Springer, Berlin, Germany, 2008), pp. 307-317.

(56) References Cited

OTHER PUBLICATIONS

Lai, "X-Ray Microfocusing Optics," Slide Presentation from Argonne National Laboratory, 71 slides, Cheiron Summer School 2007.
Langhoff et al., "X-ray Sources," Ch. 2 of "Handbook of Practical X-Ray Fluorescence Analysis," B. Beckhoff et al., eds. (Springer, Berlin Heidelberg New York, 2006), pp. 33-82.
Lechner et al., "Silicon drift detecors for high count rate X-ray spectroscopy at room temperature," Nuclear Instruments and Methods, vol. 458A (2001), pp. 281-287.
Leenaers et al., "Application of Glancing Incidence X-ray Analysis," 1997, X-ray Spectrometry, vol. 26, pp. 115-121.
Lengeler et al., "Refractive X-ray Optics," Ch. 20 of "Handbook of Optics vol. III, 2nd Ed." (McGraw Hill, New York, 2001.
Li et al., "Source-optic-crystal optimisation for compact monochromatic imaging," Proc. SPIE 5537 (2004), pp. 105-114.
Li et al., "X-ray phase-contrast imaging using cascade Talbot-Lau interferometers," Proc. SPIE 10964 (2018), pp. 1096469-1-1096469-6.
Lohmann et al., "An interferometer based on the Talbot effect," Optics Communications vol. 2 (1971), pp. 413-415.
Lühl et al., "Scanning transmission X-ray microscopy with efficient X-ray fluorescence detection (STXM-XRF) for biomedical applications in the soft and tender energy range," J. Synch. Rad. vol. 26, https://doi.org/10.1107/S1600577518016879, (2019).
MacDonald et al., "An Introduction to X-ray and Neutron Optics," Ch. 19 of "Handbook of Optics vol. III, 2nd Ed." (McGraw Hill, New York, 2001).
MacDonald et al., "Polycapillary and Multichannel Plate X-Ray Optics," Ch. 30 of "Handbook of Optics vol. III, 2nd Ed.," (McGraw Hill, New York, 2001).
MacDonald et al., "Polycapillary X-ray Optics for Microdiffraction," J. Appl. Cryst., vol. 32 (1999) pp. 160-167.
MacDonald, "Focusing Polycapillary Optics and Their Applications," X-Ray Optics and Instrumentation, vol. 2010, (Oct. 2010): 867049.
Maj et al., "Etching methods for improving surface imperfections of diamonds used for x-ray monochromators," Adv. X-ray Anal., vol. 48 (2005), pp. 176-182.
Malgrange, "X-ray Optics for Synchrotron Radiation," ACTA Physica Polinica A, vol. 82(1) (1992) pp. 13-32.
Malzer et al., "A laboratory spectrometer for high throughput X-ray emission spectroscopy in catalysis research," Rev. Sci. Inst. 89, 113111 (2018).
Masuda et al., "Fabrication of Through-Hole Diamond Membranes by Plasma Etching Using Anodic Porous Alumina Mask," Electrochemical and Solid-State Letters, vol. 4(11) (2001) pp. G101-G103.
Matsushita, "Mirrors and Multilayers," Slide Presentation from Photon Factor, Tsukuba, Japan, 65 slides, (Cheiron School 2009, Sprint-8, Japan, Nov. 2009).
Matsushita, "X-ray monochromators," Slide Presentation from Photon Factory, Tsukuba, Japan, 70 slides, (Cheiron School 2009, Spring-8, Japan, Nov. 2009).
Matsuyama et al., "Wavefront measurement for a hard-X-ray nanobeam using single-grating interferometry", Opt Express vol. 20 (2012), pp. 24977-24986.
Miao et al., "Motionless phase stepping in X-ray phase contrast imaging with a compact source," Proceedings of the National Academy of Sciences, vol. 110(48), (2013), pp. 19268-19272.
Michette, "Zone and Phase Plates, Bragg-Fresnel Optics," Ch. 23 of "Handbook of Optics vol. III, 2nd Ed.," (McGraw Hill, New York, 2001).
Mizutani et al., X-ray microscopy for neural circuit reconstruction in 9th International Conference on X-Ray Microscopy, J. Phys: Conf. Ser. 186 (2009) 012092.
Modregger et al., "Grating-Based X-ray Phase Contrast Imaging," Ch. 3 of Emerging Imaging Technologies in Medicine, M. Anastasio & P. La Riviere, ed., CRC Press, Boca Raton, FL, (2012), pp. 43-56.
Momose et al., "Biomedical Imaging by Talbot-Type X-Ray Phase Tomography" in Developments in X-ray Tomography V, Proc. SPIE vol. 6318 (2006) 63180T.
Momose et al., "Grating-Based X-ray Phase Imaging Using Multiline X-ray Source", Jpn. J. Appl. Phys. vol. 48 (2009), 076512.
Momose et al., "Phase Tomography by X-ray Talbot Interferometry for Biological Imaging" Jpn. J. Appl. Phys. vol. 45 2006 pp. 5254-5262.
Momose et al., "Phase Tomography Using X-ray Talbot Interferometer", in Synchrotron Radiation Instrumentation: Ninth International Conference, AIP Conf. Proc. vol. 879 (2007), pp. 1365-1368.
Momose et al., "Phase-Contrast X-Ray Imaging Using an X-Ray Interferometer for Biological Imaging", Analytical Sciences vol. 17 Supplement (2001), pp. i527-i530.
Momose et al., "Sensitivity of X-ray Phase Imaging Based on Talbot Interferometry", Jpn. J. Appl. Phys. vol. 47 (2008), pp. 8077-8080.
Momose et al., "X-ray Phase Measurements with Talbot Interferometry and Its Applications", in International Conference on Advanced Phase Measurement Methods in Optics and Imaging, AIP Conf. Proc. vol. 1236 (2010), pp. 195-199.
Momose et al., "X-ray Phase Imaging—From Static Observation to Dynamic Observation—", in International Workshop on X-ray and Neutron Phase Imaging with Gratings AIP Conf. Proc. vol. 1466, (2012), pp. 67-77.
Momose et al., "X-ray Phase Imaging Using Lau Effect", Appl. Phys. Express vol. 4 (2011) 066603.
Momose et al., "X-Ray Phase Imaging with Talbot Interferometry", in "Biomedical Mathematics: Promising Directions in Imaging, Therapy Planning, and Inverse Problems", Y. Censor, M. Jiang & G.Wang, eds. (Medical Physics Publishing, Madison, WI, USA, 2010), pp. 281-320.
Momose et al., "X-ray phase tomography with a Talbot interferometer in combination with an X-ray imaging microscope", in 9th International Conference on X-Ray Microscopy, J. Phys: Conf. Ser. 186 (2009) 012044.
Momose et al., "X-ray Talbot Interferometry with Capillary Plates", Jpn. J. Appl. Phys. vol. 45 (2006), pp. 314-316.
Momose et al., "Four-dimensional X-ray phase tomography with Talbot interferometry and white synchrotron radiation: dynamic observation of a living worm", Opt. Express vol. 19 (2011), pp. 8423-8432.
Momose et al., "High-speed X-ray phase imaging and X-ray phase tomography with Talbot interferometer and white synchrotron radiation", Opt. Express vol. 17 (2009), pp. 12540-12545.
Momose et al., "Phase Imaging with an X-ray Talbot Interferometer", Advances in X-ray Analysis vol. 49(3) (2006), pp. 21-30.
Momose et al.,"Demonstration of X-Ray Talbot Interferometry", Jpn. J. Appl. Phys. vol. 42 (2003), pp. L866-L868.
Momose et al.,"Phase Tomography Using an X-ray Talbot Interferometer", in Developments in X-Ray Tomography IV, Proc. SPIE vol. 5535 (2004), pp. 352-360.
Momose, "Recent Advances in X-ray Phase Imaging", Jpn. J. Appl. Phys. vol. 44 (2005), pp. 6355-6367.
Montgomery, "Self Imaging Objects of Infinite Aperture," J. Opt. Soc. Am. vol. 57(6), (1967), pp. 772-778.
Morimoto et al., "Development of multiline embedded X-ray targets for X-ray phase contrast imaging," XTOP 2012 Book of Abstracts, (Ioffe Physical—Technical Institute of the Russian Academy of Sciences, St. Petersburg, Russia, 2012), pp. 74-75.
Morimoto et al., X-ray phase contrast imaging by compact Talbot-Lau interferometer with a signal transmission grating, 2014, Optics Letters, vol. 39, No. 15, pp. 4297-4300.
Munro et al., Design of a novel phase contrast imaging system for mammography, 2010, Physics in Medicine and Biology, vol. 55, No. 14, pp. 4169-4185.
Nango et al., "Talbot-defocus multiscan tomography using the synchrotron X-ray microscope to study the lacuno-canalicular network in mouse bone", Biomed. Opt. Express vol. 4 (2013), pp. 917-923.
Neuhausler et al., "Non-destructive high-resolution X-ray imaging of ULSI micro-electronics using keV X-ray microscopy in Zernike phase contrast," Microelectronic Engineering, Elsevier Publishers BV., Amsterdam, NO, vol. 83, No. 4-9 (Apr. 1, 2006) pp. 1043-1046.
Newville, "Fundamentals of XAFS," (Univ. of Chicago, Chicago, IL, Jul. 23, 2004).

(56) References Cited

OTHER PUBLICATIONS

Noda et al., "Fabrication of Diffraction Grating with High Aspect Ratio Using X-ray Lithography Technique for X-ray Phase Imaging," Jpn. J. Appl. Phys. vol. 46, (2007), pp. 849-851.
Noda et al., "Fabrication of High Aspect Ratio X-ray Grating Using X-ray Lithography" J. Solid Mech_Mater. Eng. vol. 3 (2009), pp. 416-423.
Nojeh, "Carbon Nanotube Electron Sources: From Electron Beams to Energy Conversion and Optophononics", ISRN Nanomaterials vol. 2014 (2014): 879827.
Nuhn, "From storage rings to free electron lasers for hard x-rays", J.A37 Phys.: Condens. Matter vol. 16 (2004), pp. S3413-S34121.
Nykanen et al., "X-ray scattering in full-field digital mammography," Med. Phys. vol. 30(7), (2003), pp. 1864-1873.
Office Action received in Japanese Application No. 2016-564245, dated Oct. 23, 2018.
Oji et al., Automatic XAFS measurement system developed at BL14B2 in SPring-8, Available online Nov. 15, 2011, Journal of Synchrotron Radiation, vol. 19, pp. 54-59.
Olbinado et al., "Demonstration of Stroboscopic X-ray Talbot Interferometry Using Polychromatic Synchrotron and Laboratory X-ray Sources", Appl. Phys. Express vol. 6 (2013), 096601.
Ortega et al., "Bio-metals imaging and speciation in cells using proton and synchrotron radiation X-ray microspectroscopy," J. Royal Society Interface vol. 6 suppl. 5 (Oct. 6, 2009), pp. 6S649-6S658.
Otendal et al., A 9 keV electron-impact liquid-gallium-jet x-ray source, Rev. Sci. Instrum. vol. 79 (2008): 016102.
Oxford Instruments Inc., Series 5000 Model XTF5011 X-ray Tube information, Jun. 1998, 3 pages.
Parrill et al., "GISAXS—Glancing Incidence Small Angle X-ray Scattering," Journal de Physique IV, vol. 3 (Dec. 1993), pp. 411-417.
Paxscan Flat Panel X-ray Imaging, Varian Sales Brochure, (Varian Medical Systems, Palo Alto, CA, Nov. 11, 2004).
Pfeiffer et al., "Hard-X-ray dark-field imaging using a grating interferometer," Nature Materials vol. 7, (2008), pp. 134-137.
Pfeiffer et al., "Hard x-ray phase tomography with low brilliance x-ray sources," Phys. Rev. Lett. vol. 98, (2007), 108105.
Pfeiffer et al., "Phase retrieval and differential phase-contrast imaging with low-brilliance X-ray sources," Nature Physics vol. 2, (2006), pp. 258-261.
Pfeiffer, "Milestones and basic principles of grating-based x-ray and neutron phase-contrast imaging," in International Workshop on X-ray and Neutron Phase Imaging with Gratings AIP Conf. Proc. vol. 1466, (2012), pp. 2-11.
Pianetta et al., "Application of synchrotron radiation to TXRF analysis of metal contamination on silicon wafer surfaces," Thin Solid Films, vol. 373(1-2), 2000, pp. 222-226.
Potts, "Electron Probe Microanalysis", Ch. 10 of "A Handbook of Silicate Rock Analysis" (Springer Science + Business Media, New York, 1987), pp. 326-382 (equation quoted from p. 336).
Prewitt et al., "FIB Repair of 5X Recticles and Effects on IC Quality," Integrated Circuit Metrology, Inspection, and Process Control VII, Proc. SPIE vol. 1926 (1993), pp. 517-526.
Prewitt et al., "Focused ion beam repair: staining of photomasks and reticles," J. Phys. D Appl. Phys. vol. 26 (1993), pp. 1135-1137.
Prewitt et al., "Gallium Staining in FIB Repair of Photomasks," Microelectronic Engineering, vol. 21 (1993), pp. 191-196.
Qin et al., "Trace metal imaging with high spatial resolution: Applications in biomedicine," Metallomics, vol. 3 (Jan. 2011), pp. 28-37.
Rayleigh, "On copying diffraction gratings and some phenomena connected therewith," Philos. Mag. vol. 11 (1881), pp. 196-205.
Renaud et al., "Probing surface and interface morphology with Grazing Incidence Small Angle X-ray Scattering," Surface Science Reports, vol. 64:8 (2009), pp. 255-380.
Riege, "Electron Emission from Ferroelectrics—A Review", CERN Report CERN AT/93-18 (CERN, Geneva, Switzerland, Jul. 1993).
Röntgen, "Ueber eine neue Art von Strahlen (Wurzburg Verlag, Warzburg, Germany, 1896) also, in English, On a New Kind of Rays," Nature vol. 53 (Jan. 23, 1896). pp. 274-276.
Rovezzi, "Study of the local order around magnetic impurities in semiconductors for spintronics." PhD Dissertation, Condensed Matter, Universite Joseph-Fourier—Grenoble I, 2009, English <tel-00442852>.
Rutishauser, "X-ray grating interferometry for imaging and metrology," 2003, Eth Zurich, Diss. ETH No. 20939.
Sato et al., Two-dimensional gratings-based phase-contrast imaging using a conventional x-ray tube, 2011, Optics Letters, vol. 36, No. 18, pp. 3551-3553.
Scherer et al., "Bi-Directional X-Ray Phase-Contrast Mammography," PLoS ONE, vol. 9, Issue 5 (May 2014) e93502.
Scholz, "X-ray Tubes and Monochromators," Technical Workshop EPIV, Universitat Wurzburg (2007); 41 slides, 2007.
Scholze et al., "X-ray Detectors and XRF Detection Channels," Ch. 4 of "Handbook of Practical X-Ray Fluorescence Analysis," B. Beckhoff et al., eds. (Springer, Berlin Heidelberg, Germay, 2006), pp. 85-198.
Sebert, "Flat-panel detectors:how much better are they?" Pediatr. Radiol. vol. 36 (Suppl 2), (2006), pp. 173-181.
Shen, "Polarizing Crystal Optics," Ch. 25 of "Handbook of Optics vol. III, 2nd Ed.," (McGraw Hill, New York, 2001).
Shields et al., "Overview of Polycapillary X-ray Optics," Powder Diffraction, vol. 17(2) (Jun. 2002), pp. 70-80.
Shimura et al., "Hard x-ray phase contrast imaging using a tabletop Talbot-Lau interferometer with multiline embedded x-ray targets", Opt. Lett. vol. 38(2) (2013), pp. 157-159.
Siddons, "Crystal Monochromators and Bent Crystals," Ch. 22 of "Handbook of Optics vol. III, 2nd Ed.," (McGraw Hill, New York, 2001).
Smith, "Fundamentals of Digital Mammography:Physics, Technology and Practical Considerations," Publication R-BI-016 (Hologic, Inc., Bedford, MA, Mar. 2005).
Snigirev et al., "Hard X-Ray Microoptics," Ch. 17 of "Modern Developments in X-Ray and Neutron Optics," A. Erko et al., eds (Springer, Berlin, Germany, 2008), pp. 255-285.
Sparks Jr., "X-ray Fluorescence Microprobe for Chemical Analysis," in Synchrotron Radiation Research, H. Winick & S. Doniach, eds. (Plenum Press, New York, NY 1980), pp. 459-512.
Spiller, "Multilayers," Ch. 24 of "Handbook of Optics vol. III, 2nd Ed.," (McGraw Hill, New York, 2001).
Stampanoni et al., "The First Analysis and Clinical Evaluation of Native Breast Tissue Using Differential Phase-Contrast Mammography," Investigative Radiology, vol. 46, pp. 801-806. pub 2011-12-xx.
Strüder et al., "Silicon Drift Detectors for X-ray Imaging," Presentation at Detector Workshop on Synchrotron Radiation Instrumentation, 54 slides, (Argonne Nat'l Lab, Argonne, IL Dec. 8, 2005), available at: <http://www.aps.anl.gov/News/Conferences/2005/Synchrotron_Radiation_Instrumentation/Presentations/Strueder.pdf>.
Strüder et al., "X-Ray Detectors," Ch. 4 of "X-ray Spectrometry: Recent Technological Advances," K. Tsuji et al. eds. (John Wiley & Sons, Ltd. Chichester, West Sussex, UK, 2004), pp. 63-131.
Sun et al., "Combined optic system based on polycapillary X-ray optics and single-bounce monocapillary optics for focusing X-rays from a conventional laboratory X-ray source," Nucl. Inst. and Methods in Phys. Res. A 802 (2015) pp. 5-9.
Sun et al., "Numerical design of in-line X-ray phase-contrast imaging based on ellipsoidal single-bounce monocapillary," Nucl. Inst. and Methods in Phys. Res. A746 (2014) pp. 33-38.
Suzuki et al., "Hard X-ray Imaging Microscopy using X-ray Guide Tube as Beam Condenser for Field Illumination," J. Phys.: Conf. Ser. vol. 463 (2013): 012028.
Suzuki, "Development of the DIGITEX Safire Cardiac System Equipped with Direct conversion Flat Panel Detector," Digital Angio Technical Report (Shimadzu Corp., Kyoto, Japan, no date, published 2004 with product release).
Takahama, "RADspeed safire Digital General Radiography System Equipped with New Direct—Conversion FPD," Medical Now, No. 62 (2007).

(56) References Cited

OTHER PUBLICATIONS

Takeda et al., "Differential Phase X-ray Imaging Microscopy with X-ray Talbot Interferometer" Appl. Phys. Express vol. 1 (2008) 117002.

Takeda et al., "X-Ray Phase Imaging with Single Phase Grating", Jpn. J. Appl. Phys. vol. 46 (2007), pp. L89-L91.

Takeda et al., "In vivo physiological saline-infused hepatic vessel imaging using a two-crystal-interferometer-based phase-contrast X-ray technique", J. Synchrotron Radiation vol. 19 (2012), pp. 252-256.

Talbot, "Facts relating to optical science No IV," Philos. Mag. vol. 9 (1836), pp. 401-407.

Tanaka et al., "Cadaveric and in vivo human joint imaging based on differential phase contrast by X-ray Talbot-Lau interferometry", Z. Med. Phys. vol. 23 (2013), pp. 222-227.

Tang et al., "Micro-computed tomography (Micro-CT): a novel appraoch for intraoperative breast cancer specimen imaging," Breast Cancer Res. Treat. vol. 139, pp. 311-316 (2013).

Taniguchi et al., "Diamond nanoimprint lithography," Nanotechnology, vol. 13 (2002) pp. 592-596.

Tkachuk et al., "High-resolution x-ray tomography using laboratory sources", in Developments in X-Ray Tomography V, Proc. SPIE 6318 (2006): 631810.

Tkachuk et al., "Multi-length scale x-ray tomography using laboratory and synchrotron sources", Microsc. Microanal. vol. 13 (Suppl. 2) (2007), pp. 1570-1571.

Töpperwien et al., "Multiscale x-ray phase-contrast tomography in a mouse model of transient focal cerebral ischemia," Biomed. Op. Express, vol. 10, No. 1, Jan. 2019, pp. 92-103.

Touzelbaev et al., "Applications of micron-scale passive diamond layers for the integrated circuits and microelectromechanical systems industries," Diamond and Rel. Mat'ls, vol. 7 (1998) pp. 1-14.

Tsuji et al., "X-Ray Spectrometry: Recent Technological Acvances," John Wiley & Sons Ltd. Chichester, West Susses, UK 2004), Chapters 1-7.

Udagawa, "An Introduction to In-House EXAFS Facilities," The Rigaku Journal, vol. 6, (1) (1989), pp. 20-27.

Udagawa, "An Introduction to X-ray Absorption Fine Structure," The Rigaku Journal, vol. 11(2)(1994), pp. 30-39.

Uehara et al., "Effectiveness of X-ray grating interferometry for non-destructive inspection of packaged devices", J. Appl. Phys. vol. 114 (2013), 134901.

Viermetz et al., "High resolution laboratory grating-based X-ray phase-contrast CT," Scientific Reports 8:15884 (2018).

Vogt, "X-ray Fluorescence Microscopy: A Tool for Biology, Life Science and Nanomedicine," Presentation on May 16, 2012 at James Madison Univ., Harrisonburg, VA (31 slides), 2012.

Wan et al.,"Fabrication of Multiple Slit Using Stacked-Sliced Method for Hard X-ray Talbot—Lau Interferometer", Jpn. J. Appl. Phys. vol. 47 (2008), pp. 7412-7414.

Wang et al., "Advantages of intermediate X-ray energies in Zernicke phase constrast X-ray microscopy," Biotech. Adv., vol. 31 (2013) pp. 387-392.

Wang et al., "Non-invasive classification of microcalcifications with phase-contrast X-ray mammography," Nature Comm. vol. 5:3797, pp. 1-9 (2014).

Wang, On the single-photon-counting (SPC) modes of imaging using an XFEL source, presented at IWORLD2015.

Wang et al., "Precise patterning of diamond films for MEMS application" Journal of Materials Processing Technology vol. 127 (2002), pp. 230-233.

Weitkamp et al., "Design aspects of X-ray grating interferometry," in International Workshop on X-ray and Neutron Phase Imaging with Gratings AIP Conf. Proc. vol. 1466, (2012), pp. 84-89.

Weitkamp et al., "Hard X-ray phase imaging and tomography with a grating interferometer," Proc. SPIE vol. 5535, (2004), pp. 137-142.

Weitkamp et al., "X-ray wavefront diagnostics with Talbot interferometers," International Workshop on X-Ray Diagnostics and Scientific Application of the European XFEL, Ryn, Poland, (2010), 36 slides.

Weitkamp et al., Tomography with grating interferometers at low-brilliance sources, 2006, SPIE, vol. 6318, pp. 0S-1 to 0S-10.

Weitkamp et al., "X-ray phase imaging with a grating interferometer," Opt. Express vol. 13(16), (2005), pp. 6296-6304.

Weitkamp et al., "X-ray wavefront analysis and optics characterization with a grating interferometer," Appl. Phys. Lett. vol. 86, (2005), 054101.

Wen et al., "Fourier X-ray Scattering Radiography Yields Bone Structural Information," Radiology, vol. 251 (2009) pp. 910-918.

Wen et al., "Single-shot x-ray differential phase-contrast and diffraction imaging using two-dimensional transmission gratings," Op. Lett. vol. 35, No. 12, (2010) pp. 1932-1934.

Wobrauschek et al., "Energy Dispersive, X-Ray Fluorescence Analysis," Encyclopedia of Analytical Chemistry, R.A. Meyers, Ed. (Wiley 2010).

Wobrauschek et al., "Micro XRF of light elements using a polycapillary lens and an ultra-thin window Silicon Drift Detector inside a vacuum chamber," 2005, International Centre for Diffraction Data 2005, Advances in X-ray Analysis, vol. 48, pp. 229-235.

Wolter, "Spiegelsysteme streifenden Einfalls als abbildende Optiken fur Rontgenstrahlen" [Grazing Incidence Reflector Systems as Imaging Optics for X-rays] Annalen der Physik vol. 445, Issue 1-2 (1952), pp. 94-114.

X-ray-Optics.de Website, http://www.x-ray-optics.de/, accessed Feb. 13, 2016.

Yakimchuk et al., "Ellipsoidal Concentrators for Laboratory X-ray Sources: Analytical approaches for optimization," Mar. 22, 2013, Crystallography Reports, vol. 58, No. 2, pp. 355-364.

Yamamoto, "Fundamental physics of vacuum electron sources", Reports on Progress in Physics vol. 69, (2006), pp. 181-232.

Yanagihara et al., "X-Ray Optics," Ch. 3 of "X-ray Spectrometry: Recent Technological Advances," K. Tsuji et al. eds. (John Wiley & Sons, Ltd. Chichester, West Sussex, UK, 2004), pp. 63-131.

Yang et al., "Analysis of Intrinsic Stress in Diamond Films by X-ray Diffraction," Advances in X-ray Analysis, vol. 43 (2000), pp. 151-156.

Yashiro et al., "Distribution of unresolvable anisotropic microstructures revealed in visibility-contrast images using x-ray Talbot interferometry", Phys. Rev. B vol. 84 (2011), 094106.

Yashiro et al., "Hard x-ray phase-imaging microscopy using the self-imaging phenomenon of a transmission grating", Phys. Rev. A vol. 82 (2010), 043822.

Yashiro et al., "Theoretical Aspect of X-ray Phase Microscopy with Transmission Gratings" in International Workshop on X-ray and Neutron Phase Imaging with Gratings, AIP Conf. Proc. vol. 1466, (2012), pp. 144-149.

Yashiro et al., "X-ray Phase Imaging and Tomography Using a Fresnel Zone Plate and a Transmission Grating", in "The 10th International Conference on X-ray Microscopy Radiation Instrumentation", AIP Conf. Proc. vol. 1365 (2011) pp. 317-320.

Yashiro et al., "Efficiency of capturing a phase image using cone-beam x-ray Talbot interferometry", J. Opt. Soc. Am. A vol. 25 (2008), pp. 2025-2039.

Yashiro et al., "On the origin of visibility contrast in x-ray Talbot interferometry", Opt. Express (2010), pp. 16890-16901.

Yashiro et al., "Optimal Design of Transmission Grating for X-ray Talbot Interferometer", Advances in X-ray Analysis vol. 49(3) (2006), pp. 375-379.

Yashiro et al., "X-ray Phase Imaging Microscopy using a Fresnel Zone Plate and a Transmission Grating", in The 10th International Conference on Synchrotron Radiation Instrumentation, AIP Conf. Proc. vol. 1234 (2010), pp. 473-476.

Yashiro et. al., "Hard-X-Ray Phase-Difference Microscopy Using a Fresnel Zone Plate and a Transmission Grating", Phys. Rev. Lett. vol. 103 (2009), 180801.

Yu et al., "Morphology and Microstructure of Tungsten Films by Magnetron Sputtering," Mat. Sci. Forum, vol. 913, pp. 416-423 (2018).

(56) References Cited

OTHER PUBLICATIONS

Zanette et al., "Two-Dimensional X-Ray Grating interferometer," Phys. Rev. Lett. vol. 105 (2010) pp. 248102-1 248102-4.

Zeng et al., "Ellipsoidal and parabolic glass capillaries as condensers for x-ray microscopes," Appl. Opt. vol. 47 (May 2008), pp. 2376-2381.

Zeng et al., "Glass Monocapillary X-ray Optics and Their Applications in X-Ray Microscopy," X-ray Optics and Microanalysis: Proceedings of the 20th International Congress, AIP Conf. Proc. vol. 1221, (2010), pp. 41-47.

Zhang et al., "Application of confocal X-ray fluorescence based on capillary X-ray optics in nondestructively measuring the inner diameter of monocapillary optics," Optics Comm. (2018) https://doi.org/10.1016/j.optcom.2018.11.064.

Zhang et al., "Fabrication of Diamond Microstructures by Using Dry and Wet Etching Methods", Plasma Science and Technology vol. 15(6) (Jun. 2013), pp. 552-554.

Zhang et al., "Measurement of the inner diameter of monocapillary with confocal X-ray scattering technology based on capillary X-ray optics," Appl. Opt. (Jan. 8, 2019), doc ID 351489, pp. 1-10.

\* cited by examiner

DETECTOR FOR X-RAYS WITH HIGH SPATIAL AND HIGH SPECTRAL RESOLUTION

CROSS-REFERENCE TO RELATED APPLICATIONS

This Patent Application claims the benefit of U.S. Provisional Patent Application No. 62/206,839, filed Aug. 18, 2015 and entitled "METHOD AND APPARATUS FOR X-RAY SPECTROSCOPY WITH HIGH SPATIAL RESOLUTION", which is incorporated herein by reference in its entirety.

STATEMENT REGARDING FEDERALLY SPONSORED RESEARCH

This Application relates to work supported in part by grant number National Science Foundation (NSF) grant numbers IIP-1448727 and IIP-1556020, both entitled "Development of a Dual Energy Micro-focused X-ray Excitation Beam for Chemical Analysis and Materials Characterization". The government may have certain rights to the invention.

FIELD OF THE INVENTION

The invention disclosed herein relates to a method and apparatus for the detection and spectral analysis of x-rays emerging from specific locations within an object, and the subsequent inference of certain properties of the object, such as a mapping of the material composition or structure.

BACKGROUND OF THE INVENTION

X-ray spectrometers are used to characterize the composition of object under investigation by analyzing the x-rays emitted from the interaction of a beam of ionizing radiation (e.g. electrons, protons, x-rays) with the object. Two commonly used spectrometers are the energy-dispersive and wavelength-dispersive types, the first of which directly detects x-rays using an energy-sensitive detector system, and the second of which uses a crystal, a synthetic multilayer, or diffraction device to direct specific wavelengths toward an x-ray detector.

Often there is need to analyze a small volume within the object. In general, systems incorporating such spectrometers typically rely on the focusing of the ionizing beam to achieve high lateral resolution (the direction perpendicular to the ionizing beam axis). But, in some cases, the achievable lateral resolution is larger the incident beam size. For example, in the case of electron excitation, the beam itself may be focused to less than 200 nm, but electron scattering in the object can generate fluorescent x-rays from an interaction volume on the scale of microns.

In some approaches, x-ray optics, polycapillary light guides or collimating apertures are between the object under examination and the spectrometer to spatially limit the region from which x-rays are detected. Such approaches are frequently used to achieve high longitudinal resolution (the direction along the direction of the ionizing radiation), which is especially important when the ionizing radiation consists of x-rays which penetrates deep in the object.

Several limitations exist with such approaches. Polycapillary optics, are non-imaging optics that do not provide point-to-point imaging of the focal spot; instead, they act analogously to "wave guides" that transport x-rays generated from the first focal spot onto the second focal spot in an incoherent manner. As a consequence, resolution is still inherently limited to the "focal" spot of the polycapillary. Furthermore, the polycapillary optics are not achromatic, so any spectra of x-rays will need additional calibration for the chromatic distortion. And, although optics with smaller focal spots may be used, the collection efficiency of such smaller optics drops significantly, resulting in weak signals and very long acquisition times. Additionally, absolute quantification of material composition is difficult or impossible due to the optics not being achromatic. Other approaches include, the use of apertures or small non-imaging monocapillary x-ray optics, but these dramatically reduce the signal detected.

There is a need for a method and a spectrometer system that can efficiently collect and spatially resolve the x-rays emerging from specific region(s) within an object under examination.

BRIEF SUMMARY OF THE INVENTION

The invention disclosed herein relates to a method and spectrometer for x-ray detection and analysis of a small volume with high spatial resolution.

In particular, the invention comprises an optical imaging system comprising at least one achromatic imaging x-ray optic that collects x-rays generated within a portion (sub-volume) of an x-ray emitting volume. The achromatic imaging x-ray system is capable of forming images of x-rays of different energies at the same image plane with a predetermined magnification, just as a lens can do for visible light. The optical train of the imaging system is arranged that its object focal plane overlaps partially with the x-ray emitting volume. This enables higher resolution than the object plane focal spot size of the imaging system. The x-rays at the image plane are analyzed by an x-ray detector system with both spatial and spectral resolution.

In some embodiments of the detector system, a small aperture is placed at the image plane and upstream of an x-ray detecting element. In other embodiments, the detector system has an energy resolving pixel array x-ray detector. In some embodiments, the detector system is both position and energy sensitive, such as 1D or 2D arrays of energy dispersive detector elements.

In embodiments where spatial sensitivity is provided by one or more apertures, the energy sensitive x-ray detection system may include a spectrally sensitive but not position sensitive detector, such as a silicon drift detector (SDD), a silicon lithium (Si(Li)) detector, or any type of x-ray detector used in combination with an x-ray wavelength-dispersive component, such as a diffractive crystal or synthetic multi-layer. In some other embodiments, the detector system may comprise a diffractive element (e.g. crystal) that splits and diffracts the x-ray beam into multiple x-ray beams of different energies placed upstream of a position sensitive x-ray detector. In such embodiments, the aperture(s) are used for position sensitivity by further spatially refining the detected emitting volume of interest. Moreover, in some embodiments, the aperture(s) can be moved, which allows spatial mapping of different sub-volumes within the x-ray emitting volume.

Figure 1:
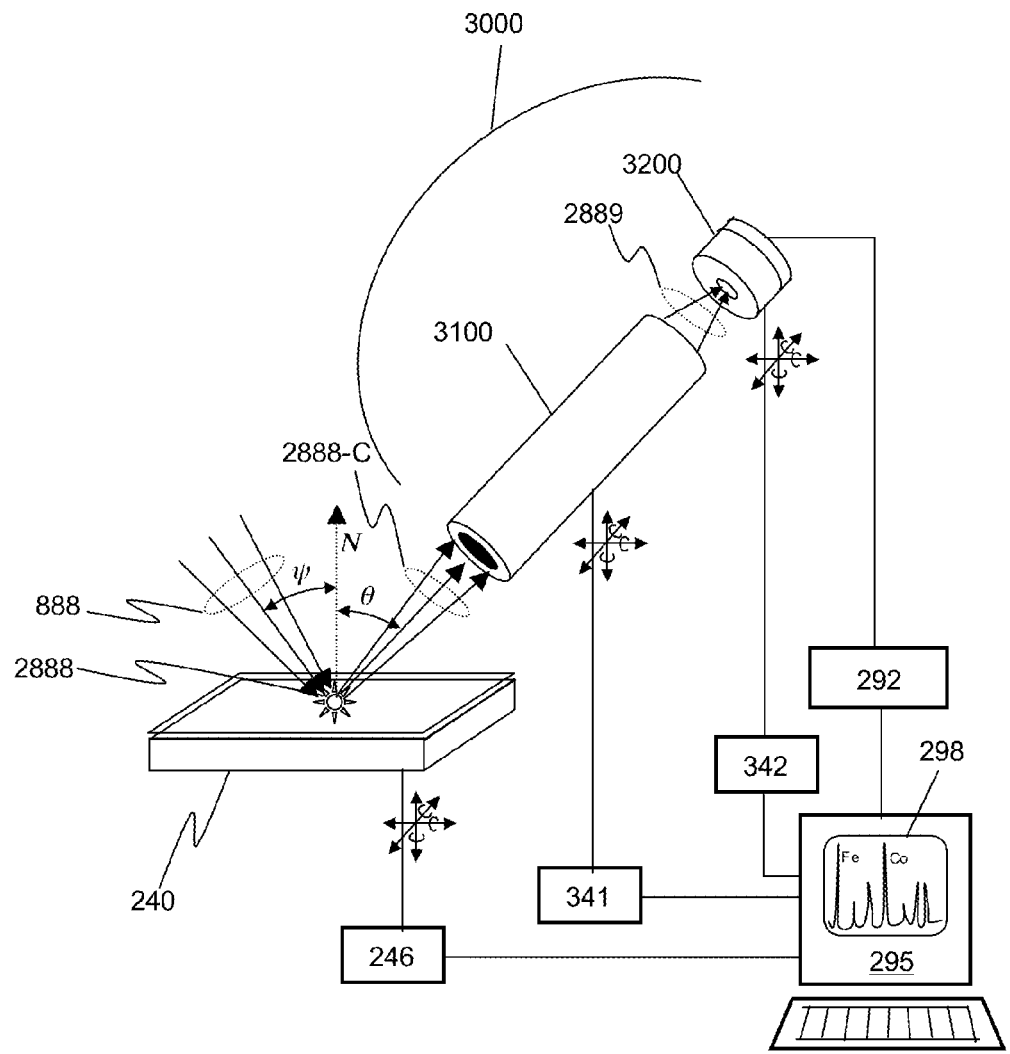
FIG. 1 illustrates a schematic diagram a fluorescence measurement system according to the invention.

Note: Elements shown in the drawings are meant to illustrate the functioning of embodiments of the invention, and should not be assumed to have been drawn in proportion or to scale.

DETAILED DESCRIPTION OF THE INVENTION

1. A Basic Embodiment

The invention disclosed herein relates to a method and apparatus for x-ray detection with high spatial resolution and spectral energy resolution. Spatial resolution is achieved in part through the use of achromatic x-ray imaging optics between a object and a detector system placed at the image plane capable of spectral resolution while spatially resolving the image formed by the optics. Spectral resolution is achieved through the use of energy sensitive detectors or by using other x-ray spectroscopy techniques based on energy-selective elements, such as crystal monochromators, filters, or multilayer reflectors. Spatial sensitivity is achieved either through use of a spatially selective aperture or an array arrangement of the energy-resolving elements.

FIG. 1 illustrates a schematic of the basic elements of a simple embodiment of the invention. An x-ray spectrometer system 3000 is placed to collect x-rays 2888 emitted within a sub-volume of an object 240. These x-rays are generated through the interaction of a source of x-ray excitation (e.g. electrons, protons, x-rays) 888 that may be focused, as shown, or unfocused with the object 240. The x-ray spectrometer system 3000 comprises an optical train 3100 and an x-ray detector system 3200. The optical train 3100 produces a converging wavefront 2889 that forms an x-ray image of the object at the x-ray detector system 3200.

The x-ray detector system 3200 detects a portion of the x-ray image and converts the detected x-rays to electronic signals. In general, a spatially sensitive method, such as the use of an aperture in combination with an energy-sensitive detector arrangement or by arranging multiple energy-sensitive elements in an array, is included in the x-ray detector system 3200 to enable position sensitivity. Such a detector may include a silicon drift detector that allows the determination of both x-ray count and energy. The electronic signals may be further processed by signal processing electronics 292 and passed to an analysis system 295, which may comprise a display 298.

By forming an image of the x-rays emerging from the object 240 onto the detector plane of the detector system, x-rays corresponding to a specific position in the object are converted into electronic signals by the x-ray detection system 3200. The exact position on the object being imaged may be adjusted in a number of ways to allow a "map" of the detected x-ray properties to be created. Translation and rotation controls 246 for the object 240 may be provided, to allow different positions on the object 240 to be detected in a systematic scan, and for the object 240 to be brought into the focus range of the optical train 3100. Likewise, translation and rotation controls 341 for the optical train 3100 itself and/or translation and rotation controls 342 for elements (such as spatially selective apertures) in the detection system 3200 may also be provided.

In this illustration, given a local surface normal N in the region of the object 240 to be observed, the axis of the optical train is aligned to be at an angle $\theta$ relative to the local surface normal N. As illustrated, $\theta$ is approximately 45° but may vary anywhere from near 0° to at or near 90° relative to the surface normal. This angle $\theta$ may be changed to larger angles (e.g. 60°-80°) so that the x-ray spectrometer system 3000 collects x-rays produced in planes that are near-parallel to the object surface. This allows mapping of x-rays emitted as a function of depth and may be useful for such applications as when thin films or sample layers are of interest. Alternatively, placing the detector system to have a smaller value of $\theta$ (e.g. 0°-20°) allows mapping laterally across the object.

Likewise, as illustrated, the source of excitation 888 is shown as being incident on the object 240 at an angle $\psi$ of approximately 45°, but may vary anywhere from near 0° to at or near 90° relative to the surface normal. The source of excitation likewise can be focused, as shown, or not focused. This angle $\psi$ may be changed to larger angles (e.g. 60°-80°) or smaller angles (e.g. 0°-20°), or may even excite the object 240 from the opposite side (i.e. with $\psi$ ranging from 90° to 270°). This angle of incidence may or may not be in the same plane as the plane containing the local surface normal N and the collection angle $\theta$. As illustrated, the geometry is one that would be used for fluorescence detection under excitation by higher energy x-rays or electrons; however, the excitation may be due to a number of sources (e.g. electrons, protons, x-rays, gamma rays, etc.), and the spectrometer system 3000 may be aligned to collect any of a number of x-rays emerging from the object (e.g. x-rays from fluorescence, transmitted or reflected x-rays, scattered or diffracted x-rays, etc.), depending on the information desired about the object.

Figure 2:
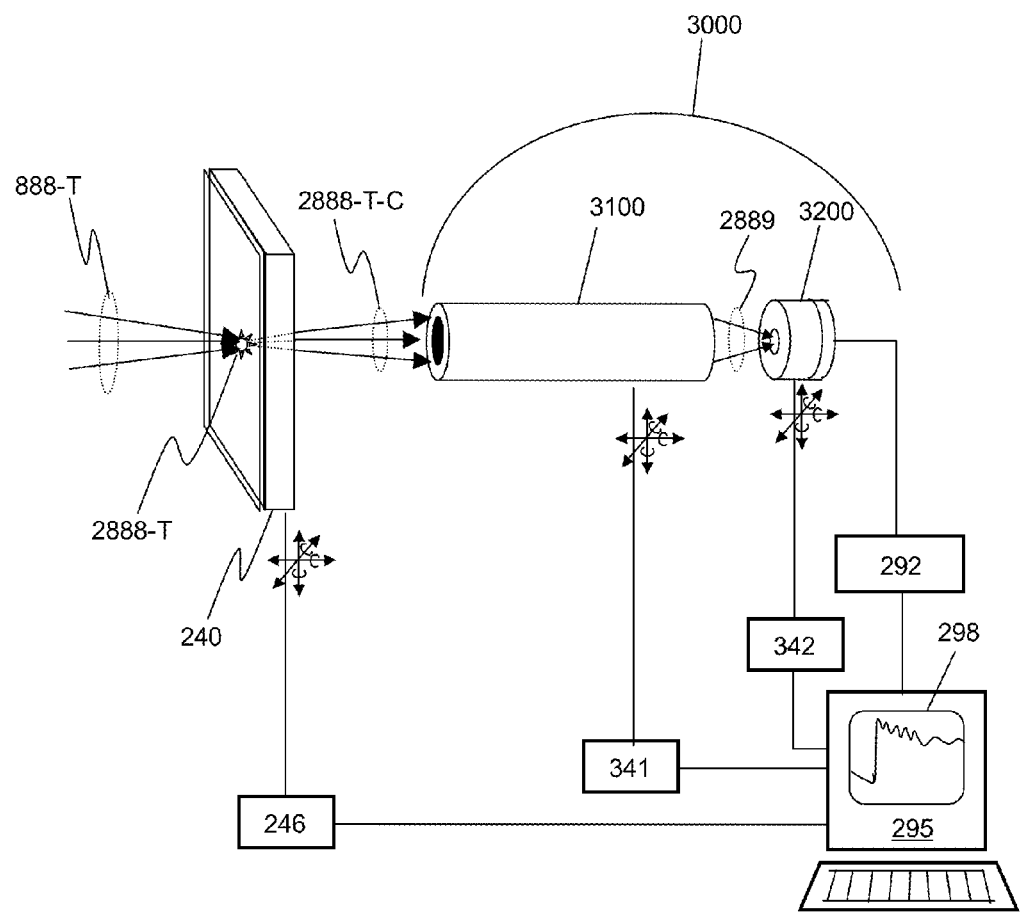
FIG. 2 illustrates a schematic diagram an x-ray transmission measurement system according to the invention.

In FIG. 2, another embodiment is shown, in which the initial x-rays 888-T are incident on the object 240 on the opposite side of the position of the x-ray spectrometer system 3000. In this embodiment, both transmission x-ray imaging information and x-ray fluorescence imaging information can be acquired simultaneously to enable complementary information on the structure and composition of a object. The x-rays that are of interest here are x-rays 2888-T, of which a portion 2888-T-C are collected by the x-ray spectrometer system 3000. These x-rays 2888-T may comprise x-rays arising from several phenomena, including x-ray transmission and x-ray fluorescence.

As before, once the x-rays are collected, the optical train 3100 forms a converging wavefront 2889 that forms an image at the x-ray detection system 3200. As before, motion of the object 240, the optical train 3100, or the x-ray detection system 3200 (such as aperture placement) may be controlled by controllers 246, 341, 342 respectively separately or on combination. The position and energy sensitivity of the detection system is achieved either through the use of an aperture in combination with at least one energy resolving x-ray detector, or through the use of detectors with both spatial and energy resolving capabilities, such as arrayed detectors of energy-resolving elements.

Figure 3:
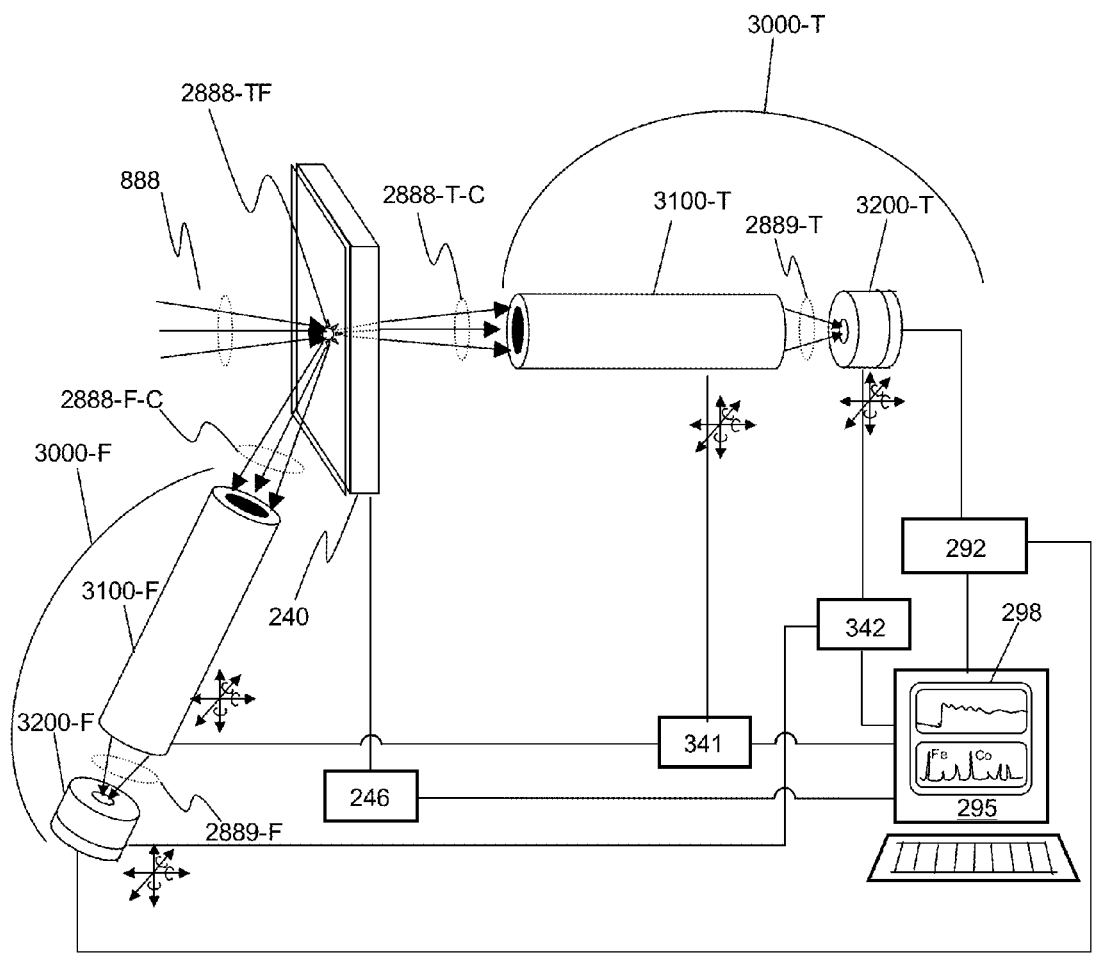
FIG. 3 illustrates a schematic diagram a combined x-ray fluorescence and x-ray transmission measurement system according to the invention.

In some embodiments, multiple detector systems may be used simultaneously to detect different properties of an object or to further refine the spatial resolution of the system by triangulating the signal from multiple angles. FIG. 3 illustrates an object 240 being irradiated with incident x-rays 888, and the simultaneous use of a first x-ray spectrometer system 3000-T according to the invention aligned to measure x-rays 2888-T and a second x-ray spectrometer system 3000-F according to the invention to measure fluorescent x-rays 2888-F radiated from the surface of the object 240. The various reference numbers in FIG. 3 correspond to their equivalents in the previous drawings, with the suffix "-T" added for components for the collection and measurement of x-rays 2888-T-C, and the suffix "-F" added for components for the collection and measurement of fluorescent x-rays 2888-F-C. As illustrated, translation and rotation controls 341 and 342 respectively control motions for the corresponding elements in both of the two detection systems, to better coordinate that both systems are observing x-rays emerging from the same position, and signal processing electronics 292 as shown now collects information from both detectors for processing. However, embodiments in which each detector is independently controlled and managed may also be designed.

Although FIG. 3 illustrates two detectors being deployed on opposite sides of an object, positioning multiple detectors on the same side of an object to measure, for example, fluorescence at different angles may be deployed in arrangements similar to that illustrated in FIG. 1, in which the value of θ is different for the two detectors. Likewise, embodiments with multiple detectors having the same value of θ relative to the surface normal, but viewing the object from different directions, may also be designed.

2. Additional Details for Embodiments of the Invention

Figure 4:
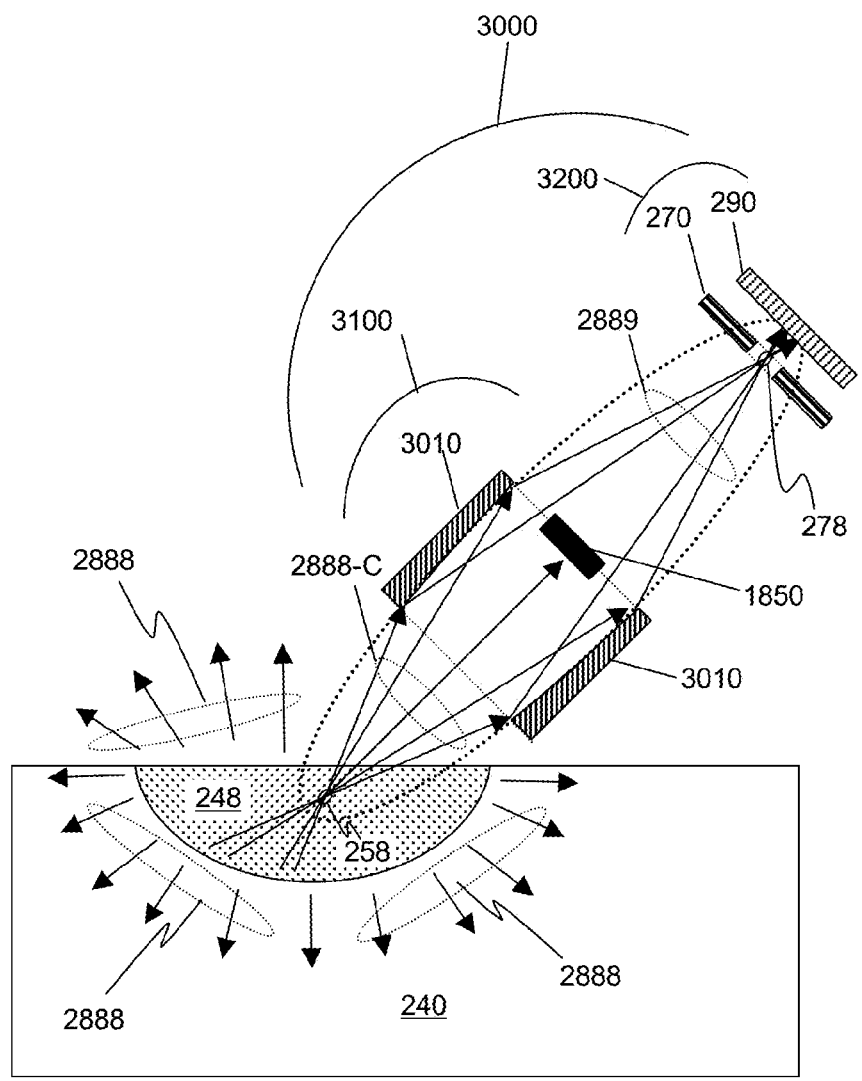
FIG. 4 illustrates a cross-section schematic diagram of an x-ray measurement system according to an embodiment of the invention.

FIG. 4 illustrates an embodiment of the invention in more detail.

In FIG. 4, an object 240 radiates x-rays 2888 from an x-ray production region 248. As shown, the x-rays are fluorescence x-rays emerging from the object 240, as were also illustrated in FIG. 1, but the spectrometer system 3000 may be used for x-rays with other origins as well.

The x-ray spectrometer system 3000 is aligned to collect a portion 2888-C of the x-rays 2888 being radiated from the object 240. The x-ray spectrometer system 3000 comprises two main components: an optical train 3100, and an x-ray detection system 3200.

In this embodiment, the optical train 3100 comprises an axially symmetric achromatic x-ray reflecting optic 3010 having the topology of a portion of a hollow tube. The inner surface of the reflecting optic in general will be shaped in the form of a quadric surface, and in the embodiment illustrated in FIG. 4, the surface is an ellipsoid.

The x-ray reflecting optic 3010 is positioned such that one of the foci 258 of the ellipsoidal shape overlaps the x-ray production region 248 within the object 240, while the other of the foci is positioned at the entrance to the x-ray detection system 3200. Note that in some embodiments (not shown), the first focus and point spread function of the optic may encompass the entire x-ray generating volume 248, or as in the case of the figure, may be smaller. The ellipsoidal optic 3010 therefore collects x-rays 2888-C diverging from the object 240, and focuses them into a converging wavefront 2889 into an image at the x-ray detection system 3200.

As shown, the optical train 3100 also comprises a beam stop 1850 that blocks on- or nearly-on-axis x-rays that do not intersect with the quadric surface.

Although the optical train in FIG. 4 is shown creating a 1:1 mapping between the x-rays emerging from a point in the object and the corresponding point in the image plane, optical trains that produce magnified images may also be designed. Magnification factors from 1× to 20× may be used for a variety of x-ray analysis applications, and for some applications, magnification as large as 1000× may be used. Likewise, although an achromatic system of any resolution can be used, for better spatial selectivity, an optical train forming an image with a point spread function (measured at full-width half maximum (FWHM)) of 20 micrometers or less (e.g. <5 microns) is preferred. In some embodiments, the point spread function of an optical element in the optical train may range from less than 0.1 micrometers to 3 micrometers. The field of view of the image is ideally at least 2× the point spread function. And, although simple total external reflection from a glass surface or a coated surface (e.g. glass internally coated with platinum) may be the mechanism of reflection for the quadric surface of the optic, surfaces with multilayers may also be used to provide additional reflectivity and/or beam conditioning (e.g. monochromatization) benefits. More details on this and other x-ray optical systems that may be used to form x-ray images have been described in the co-pending U.S. Patent Application entitled X-RAY ILLUMINATORS WITH HIGH FLUX AND HIGH FLUX DENSITY by the inventors of the present invention (U.S. patent application Ser. No. 14/544,191 filed Dec. 5, 2014), which is hereby incorporated by reference in its entirety, along with the provisional Applications to which it claims priority.

The x-ray detection system 3200 comprises an aperture element 270 comprising an aperture 278, and an x-ray detector 290. In this figure, the aperture 278 is shown to be positioned corresponding to the second of the foci of the ellipsoidal surface of the x-ray reflecting optic 3010, which also corresponds to the image plane, so that only x-rays emerging from the point 248 within the object 240 corresponding to the first focus will pass through the aperture and produce a signal from the x-ray detector 290. The use of an aperture with a smaller point spread function than the optical train allows higher spatial resolution.

The aperture element 270 may be a simple metal film with a hole to form the aperture, or may be a patterned material, in which certain regions have been thinned or comprise materials with low x-ray absorption properties (e.g. carbon fiber, aluminum, etc.) to provide regions that transmit more x-rays. The size and shape of the aperture may be selected to correspond to the size and shape of the region of interest in the object under examination. The dimensions of the aperture may be as small or smaller than the point spread function of the optical train 3100, and may be as small as 0.1 micrometers, or may be larger if larger areas of the object are under examination. The aperture may have the shape of a circle, a slit, a square, a cross, a diamond, an annulus, or a custom designed shape to match particular predetermined shapes that may be anticipated to be found in the object. The aperture may be positioned to be along the optical axis of the achromatic optical train 3100, but embodiments in which the aperture is placed off-axis may also be designed to only select the portion of the image formed at the second focus 278. An example may be to select only x-rays corresponding to the surface of a sample for thin film or corrosion analysis. Embodiments in which the aperture is also moved to sample different positions in the image plane may also be designed. The aperture may be displaced to allow mapping of x-rays along or orthogonal to the optical axis of the achromatic optical train 3100. Additionally or alternatively, the relative distance between the object and the aperture is varied while the configuration of the aperture and the energy dispersive detector or the wavelength spectrometer is unchanged, to map the x-ray spectra of the x-ray emitting volume along the axis of the achromatic optical train 3100. Effectively varying the distance between the object and the aperture is equivalent to changing the image conjugate of the achromatic optical train 3100, or changing the distance between the object plane and the image plane.

In some embodiments, the detector 290 may be an energy dispersive x-ray spectrometer (EDS), such as a silicon drift detector, lithium drifted silicon (SiLi) detector, germanium (GeLi), silicon PIN, or x-ray microcalorimeter, placed downstream of the aperture to receive, analyze, and generate a spectrum of the x-rays passing through the aperture. Such detectors are well known in the art and are capable of energy resolution.

Detector geometries and arrangements for x-ray fluorescence may be known to those skilled in the art. For more on x-ray detectors, see Albert C. Thompson, "X-Ray Detectors", Section 4.5 of the X-ray Data Booklet (xdb.lbl.gov/Section4/Sec_4-5.pdf).

3. Wavelength Selective Detector Systems

Figure 5:
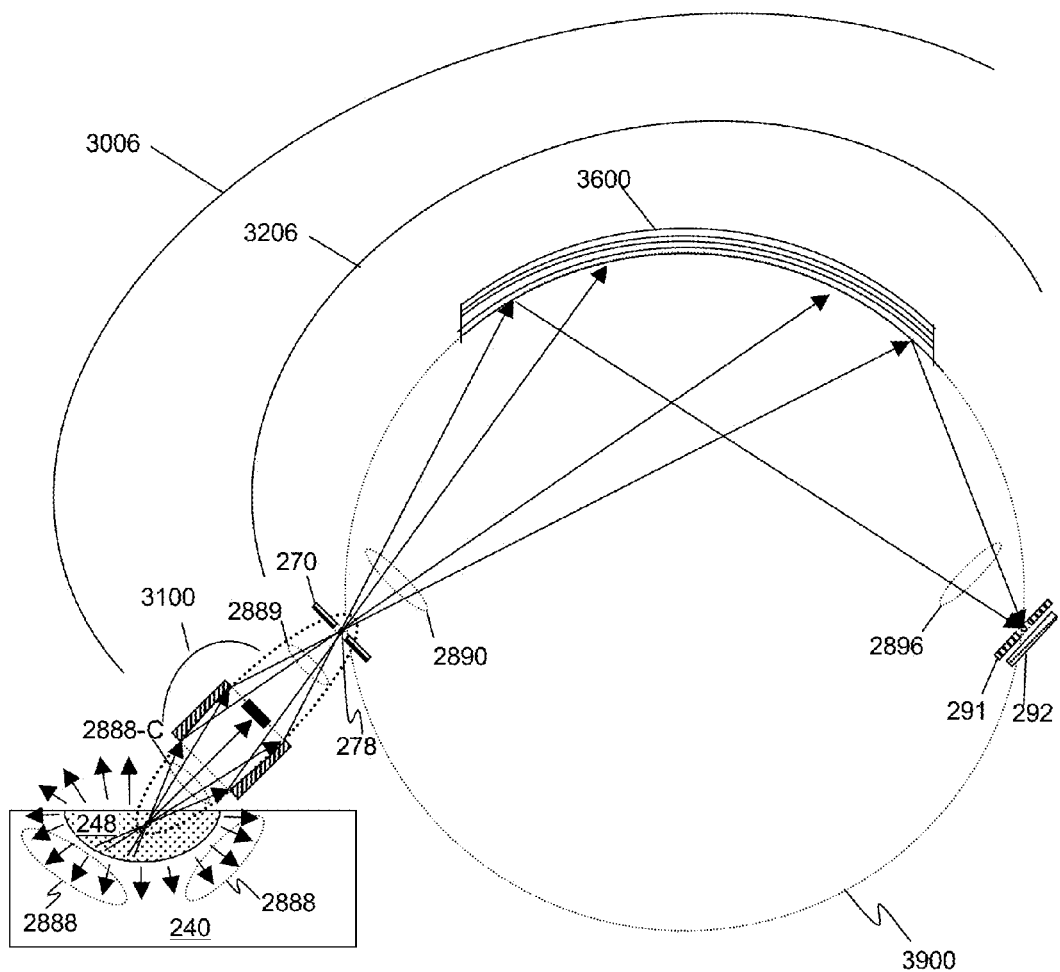
FIG. 5 illustrates a cross-section schematic diagram of an x-ray measurement system using a wavelength dispersive detector system according to an embodiment of the invention.

FIG. 5 represents another embodiment having x-ray spectrometer system 3006 in which the optical train 3100 remains the same as in FIG. 4, but the x-ray detection system 3206 now has a wavelength dispersive element (in this example, a curved Bragg reflector) instead of a silicon drift detector. In this embodiment, the aperture 278 is placed at one position on a Rowland Circle 3900, a configuration known to those skilled in the art of x-ray spectroscopy, and a curved reflector 3600 is also placed along the Rowland circle. The diffractive element 3600 will take x-rays 2890 diverging from the aperture 278, intersect them and redirect those intersecting the crystal at the Bragg angle to converge on a point at a second location on the Rowland circle 3900. Exemplary diffractive elements include crystals of Johansson curvature (as shown) or of Johann curvature. As illustrated, this second location may have an additional aperture element 291 and detector 292. Relative motion of the aperture 278, diffractive element 3600, and detector 292 along the Rowland Circle allows for x-rays of different wavelengths diffracting from the curved reflector to be detected. The detector 292 may be any detector capable of detecting x-rays, but is most commonly a gas proportional counter type. In some embodiments, the detector 292 may be a position sensitive detector such as a CCD-based detector.

Figure 6:
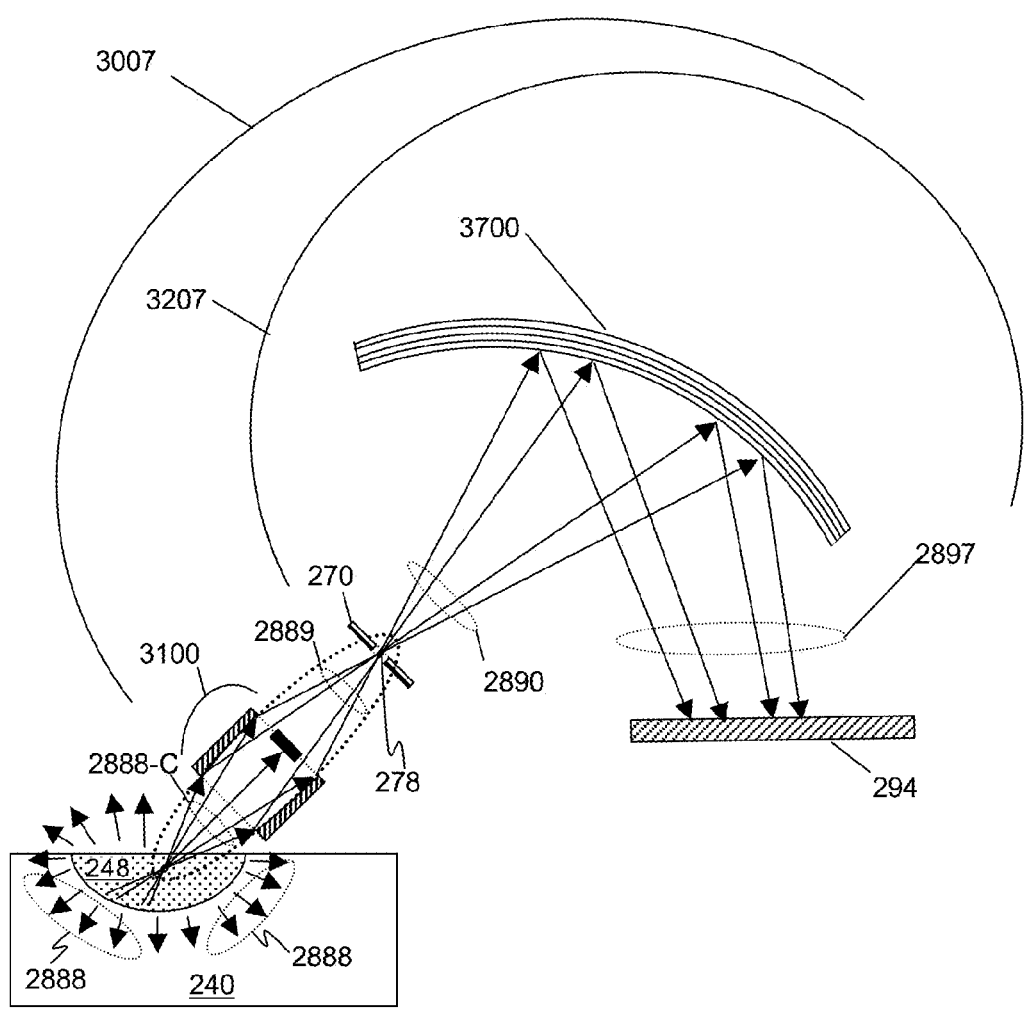
FIG. 6 illustrates a cross-section schematic diagram of an alternative x-ray measurement system using a detector system comprised of a dispersive element in combination with a position-sensitive detector according to one embodiment of the invention.

An alternative embodiment is illustrated in FIG. 6. In this embodiment of the x-ray spectrometer system 3007, a wavelength dispersive element 3700 is also used in the detector system 3207. In this embodiment, the dispersive element 3700, is a concave spherical Bragg reflector that disperses the x-ray beam so that different wavelengths propagate at different angles. This dispersed x-ray beam 2897 falls on a position sensitive detector 294, in which different positions correspond to different wavelengths, and the signals from pixels at these positions correspond to the intensities of the associated wavelength.

Although the dispersive element 3700 is illustrated as a concave reflector, in some embodiments, a planar Bragg diffractive reflector may be more suitable, and in other embodiments, a convex reflector may be used. In other embodiments, a von Hamos wavelength spectrometer comprising a cylindrically bent crystal may be used as the diffractive element.

Figure 7:
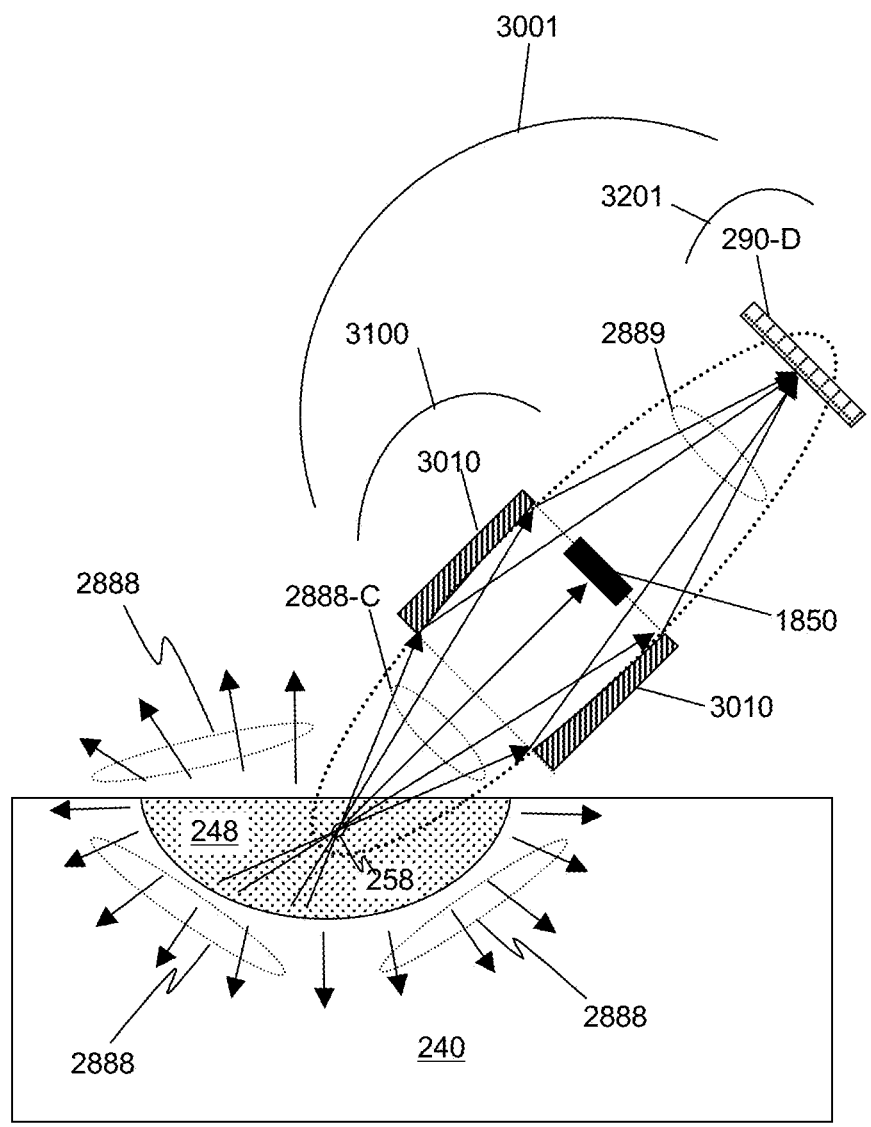
FIG. 7 illustrates a cross-section schematic diagram of an x-ray measurement system using a position-sensitive x-ray detector according to an embodiment of the invention.

FIG. 7 illustrates an additional embodiment of an x-ray spectrometer system 3001, in which the optical train 3100 is the same as in previous embodiments, such as illustrated in FIG. 4, but the x-ray detection system 3206 comprises a position and energy sensitive detector 290-D, such as a 2-D x-ray array detector of energy dispersive elements. In this embodiment, the image from the optical train 3100 is formed directly on the position x-ray array detector 290-D. Each pixel serves to detect x-rays from a specific position in the object, and there is therefore no need to use an additional aperture to provide spatial selectivity.

For such a detector, a pixel-array energy dispersive spectrometer, such as a pnCCD x-ray color camera, such as that produced by PNDetector GmbH of Munich, Germany, the Maia detector array system, or a micro-array calorimeter, may be used. Each pixel in such a detector is capable of detecting and analyzing the spectrum of x-rays incident upon it, and there is no need for an additional aperture to provide spatial selectivity.

As in the previously described embodiments, the optical train 3100 in this embodiment may provide a 1:1 size ratio between the object and the image, or may be designed to produce a magnified image, with a magnification factor from 1× to 20×.

4. Wavelength Selective Optical Trains

Figure 8:
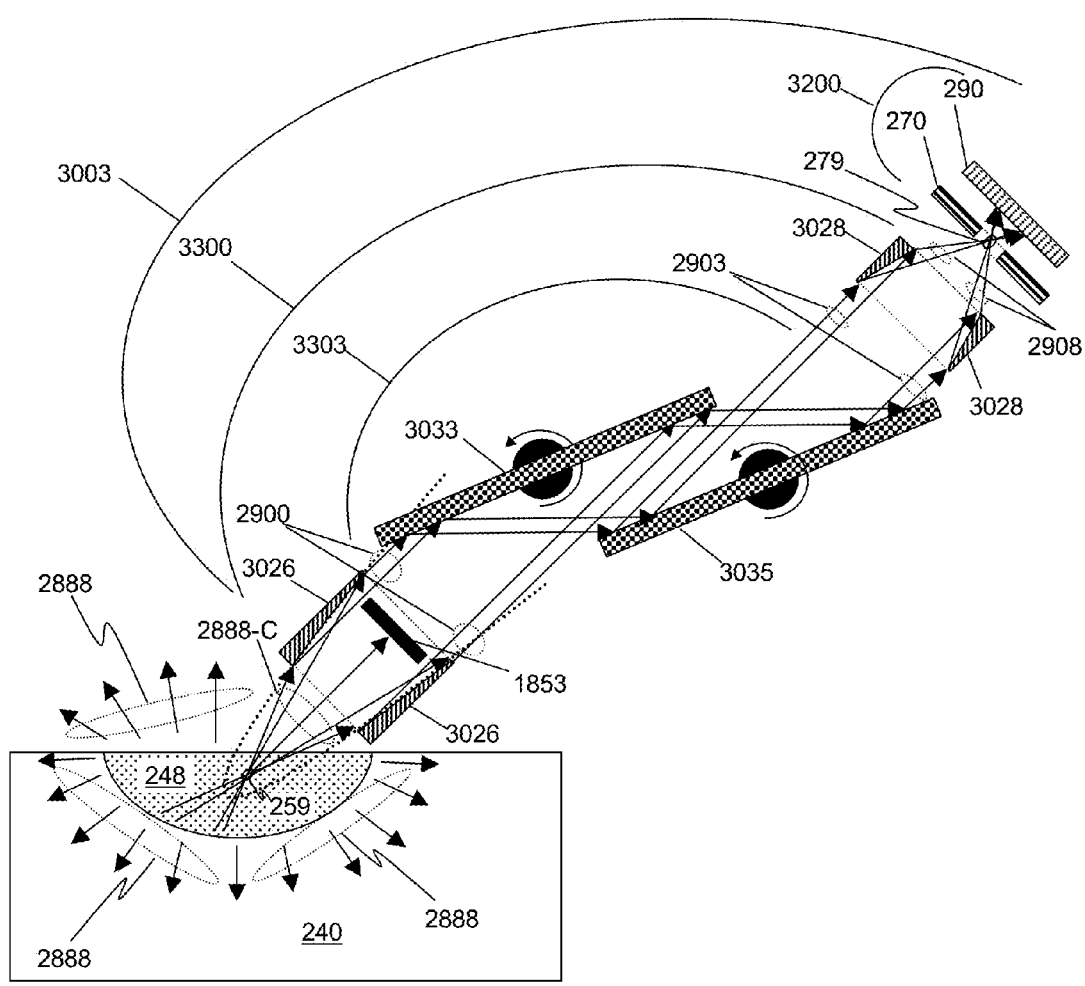
FIG. 8 illustrates a cross-section schematic diagram of an x-ray measurement system using a double crystal monochromator in the optical train according to one embodiment of the invention.

In some embodiments of the invention, the optical train may be modified to also include spectral selectivity. FIG. 8 illustrates an embodiment of the invention in which a double crystal monochromator 3303 has been used in the optical train to provide spectral selectivity.

As in the previously described embodiments of the invention, an object 240 radiates x-rays 2888 from an x-ray production region 248.

The x-ray spectrometer system 3003 is aligned to collect a portion 2888-C of the x-rays 2888 being radiated from the object 240 and, as in the previous embodiments, the x-ray spectrometer system 3003 comprises two main components: an optical train 3300 and an x-ray detection system 3200.

However, in this embodiment, the optical train comprises two axially symmetric achromatic x-ray reflecting optics 3026 and 3028 each having an inner surface in the form of a paraboloid.

The first paraboloidal optic 3026 is positioned such that the focus 259 of the paraboloid is within the region 248 radiating x-rays. X-rays 2888-C collected from this focus by the paraboloid optic 3026 then form a collimated x-ray beam 2900. As shown, the optical train 3300 also comprises a beam stop 1853 that blocks on- or nearly-on-axis x-rays that do not intersect with the paraboloidal surface, and are therefore will not be aligned with the collimated x-rays 2900.

The collimated beam 2900 is then diffracted through a double crystal monochromator 3303. This monochromator 3303 comprises two planar Bragg diffraction crystals 3033 and 3035 arranged with respect to the collimated beam such that only x-rays of a certain wavelength are reflected from both of the crystals and emerge as a collimated monochromatic beam 2905. Adjusting the angle of the crystals relative to the collimated beam 2900 allows the selection of a particular wavelength. Although a double crystal monochromator is shown, other wavelength selective elements may be used in the optical train, such as channel cut crystals or even single crystals (curved or planar) or a single multilayer reflector. However, in the latter cases, the two optical elements would not have parallel optical axes.

The collimated monochromatic x-rays 2903 are then collected by a second paraboloidal reflecting optic 3028, focusing the x-rays into a converging beam 2908 that forms an image on the x-ray detection system 3200.

As in previous embodiments, the x-ray detection system 3200 comprises an aperture element 270 comprising an aperture 279, and an x-ray detector 290. This aperture 279 is positioned in front of the x-ray detector 290. The detector is positioned to correspond to the focus of the paraboloidal surface of the second x-ray reflecting optic 3028, so that only monochromatic x-rays emerging from the point 249 within the object 240 corresponding to the first focus will pass through the monochromater and the aperture to produce a signal from the x-ray detector 290.

As before, in some embodiments, the detector 290 may be an energy dispersive x-ray spectrometer (EDS), such as a silicon drift detector, or x-ray microcalorimeter, placed downstream of the aperture to receive, analyze, and generate a spectrum of the x-rays passing through the aperture. In some embodiments, this detector 290 may be a wavelength dispersive detector system comprising a diffractive element and an x-ray detector, such as the one illustrated in the embodiment of FIG. 5.

The embodiment comprising a monochromator as illustrated in FIG. 8 is useful for selecting a particular wavelength of x-rays for observation, and for scanning the wavelength to produce spectra of the x-rays collected from the focus spot 259. However, in other embodiments, instead of selecting only a particular x-ray wavelength for observation, it may be desirable detect a broad spectrum of x-rays, with only a few wavelengths rejected. For example, if viewing x-ray fluorescence from a material comprising iron and other elements, the iron fluorescence can dominate the signal and saturate the detectors. Therefore, a "notch" filter to reject only the iron fluorescence may be desirable.

Figure 9:
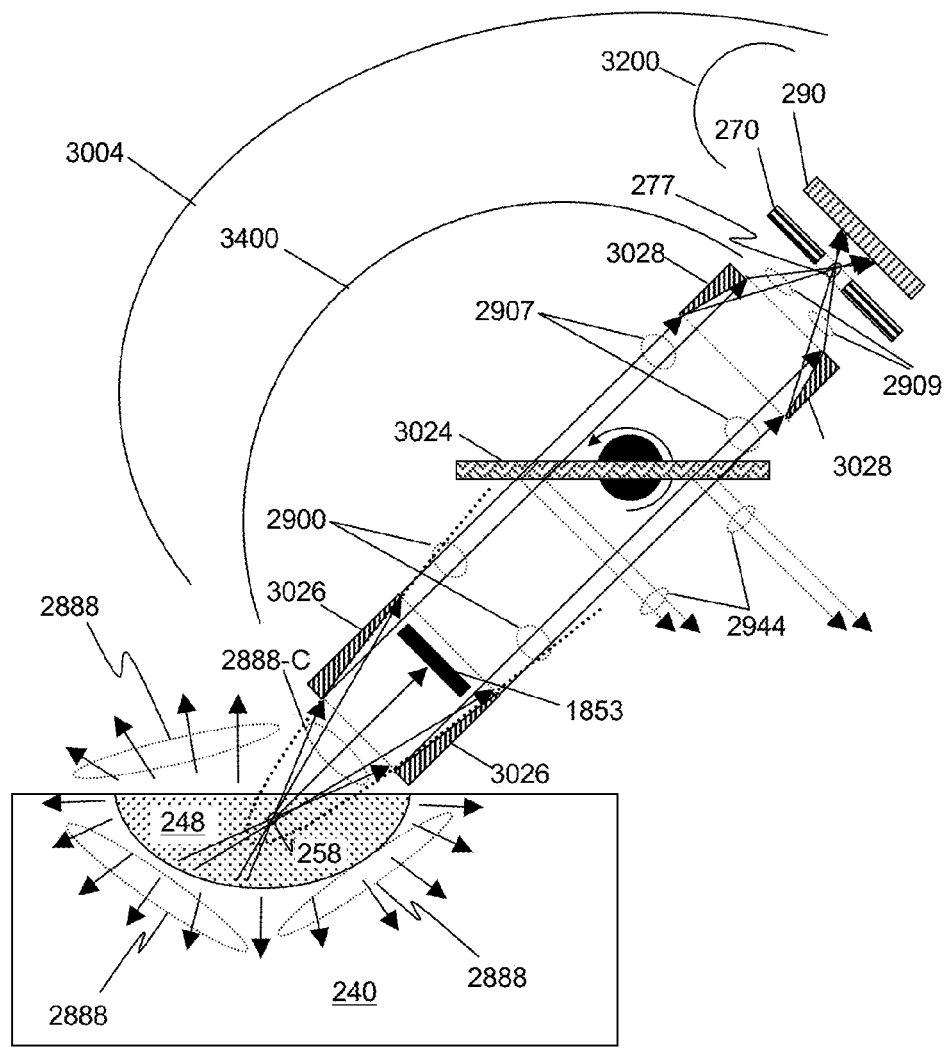
FIG. 9 illustrates a cross-section schematic diagram of an x-ray measurement system using a selective x-ray rejection device in the optical train according to one embodiment of the invention.

FIG. 9 illustrates an embodiment of an x-ray spectrometer system 3004 incorporating a spectral conditioning element 3024 in the optical train 3400.

As in the embodiment incorporating the monochromator described above, an object 240 radiates x-rays 2888 from an x-ray production region 248. As discussed above, this x-ray production region 248 may be radiating transmitted x-rays, or fluorescence x-rays, or x-rays from any number of phenomena.

The optical train 3400 is aligned to collect a portion 2888-C of the x-rays 2888 being radiated from the object 240 using an achromatic first paraboloidal optic 3026 positioned such that the focus 259 of the paraboloid is within the region 248 radiating x-rays. X-rays 2888-C collected from this focus by the paraboloid optic 3026 then form a collimated x-ray beam 2900. As shown, the optical train 3300 also comprises a beam stop 1853 that blocks on- or nearly-on-axis x-rays that do not intersect with the parabolic surface.

The collimated beam 2900 then propagates through an x-ray conditioning element 3024. This conditioning element 3024 may comprise an x-ray spectral filter placed between the x-ray emitting volume and the aperture that rejects a predetermined wavelength of x-rays with a certain spectral bandwidth from reaching the x-ray detection system. The x-ray spectral filter may be a thin film (foil) filter that contains an element that has an x-ray absorption edge slightly below the predetermined x-ray wavelength. The x-ray spectral filter may be a low-Z, high transmission material, such as silicon (Si), lithium (Li), or diamond or graphite (C). Alternatively, the x-ray spectral conditioning element may comprise a wavelength dispersive component, such as a crystal or synthetic multilayer, which is configured to diffract a narrow bandwidth of x-rays centered on the predetermined wavelength of x-rays to be rejected, and is sufficiently thin to have high transmission for the x-rays of other wavelengths. For such a diffractive element, a means for turning the angle of the filter relative to the direction of collimated x-ray propagation may also be provided. As shown in FIG. 9, the rejected x-rays 2944 are diffracted away from the optical train 3400 to remove them from detection.

The collimated filtered x-rays 2907 are then collected by a second achromatic paraboloidal reflecting optic 3028, which focuses the x-rays into a converging beam 2908 that forms a focus on the x-ray detection system 3200.

More detailed descriptions of x-ray gratings and monochromators may be may be known to those skilled in the art. For more on x-ray gratings and monochromators, see Malcolm R. Howells, "Gratings and Monochromators", Section 4.3 of the X-ray Data Booklet (xdb.lbl.gov/Section4/Sec_4-3Extended.pdf).

5. Position Selectivity by Selective Object Illumination

For the embodiments described so far, the optical train forms an image of x-rays collected by optics with a quadric surface from a specific point of focus in the x-ray radiating region, and forms an image of that spot at the detector. The embodiments are therefore selective in lateral position, allowing 2-D "maps" of object properties to be formed as the object and/or spectrometer are laterally translated to view different spots on the object.

However, although there is some lateral selectivity with the use of x-ray imaging optics, x-rays not only from the point of focus, but from anywhere along the collection cone of the quadric optic may be collected and passed on to the detector, even if only in the form of an out of focus image.

Selectivity in depth may be additionally achieved if the x-ray emitting region is limited by selective excitation at certain depths within the object.

Figure 10:
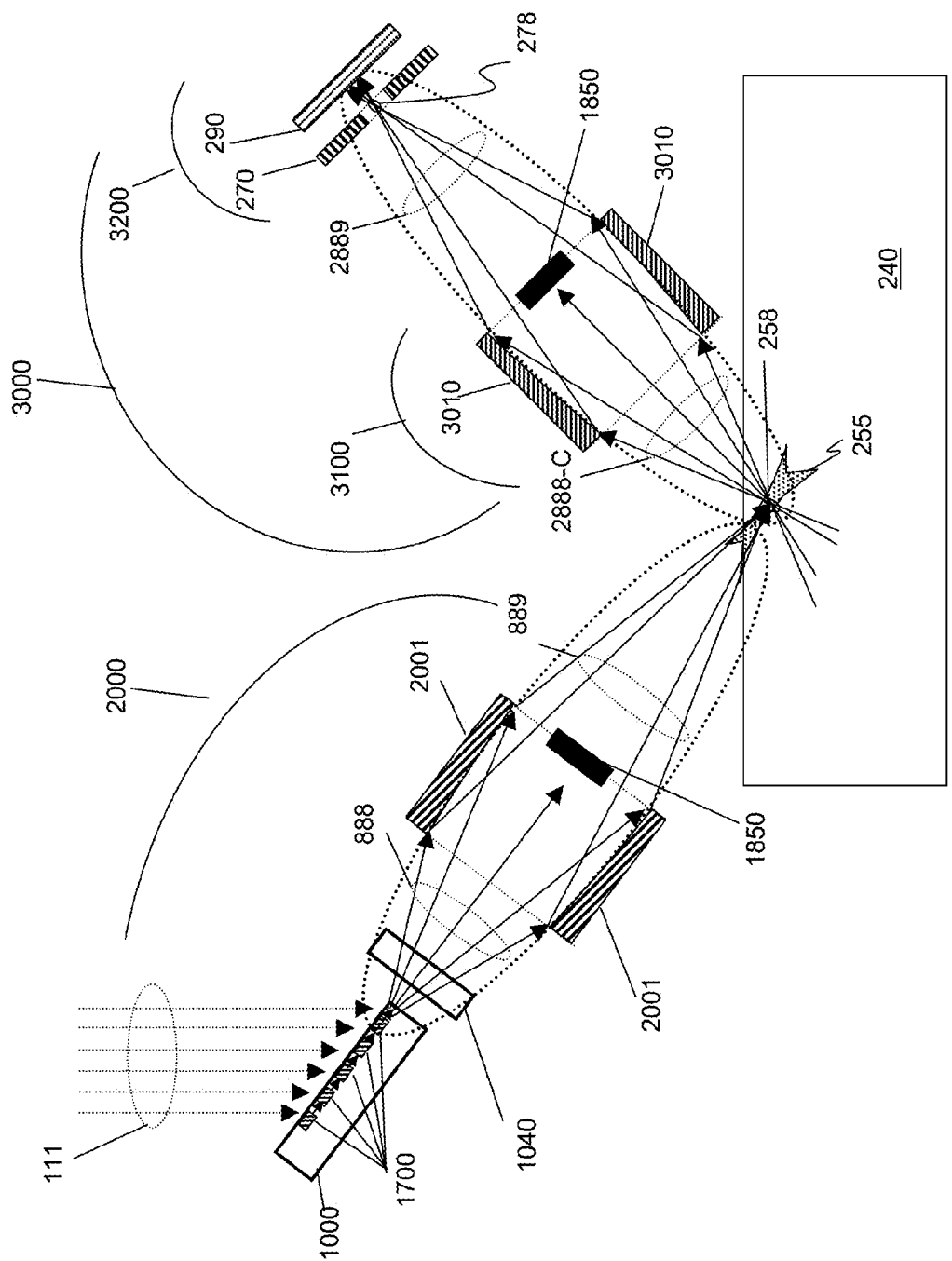
FIG. 10 illustrates a cross-section schematic diagram of a confocal x-ray measurement system according to one embodiment of the invention.
Figure 11:
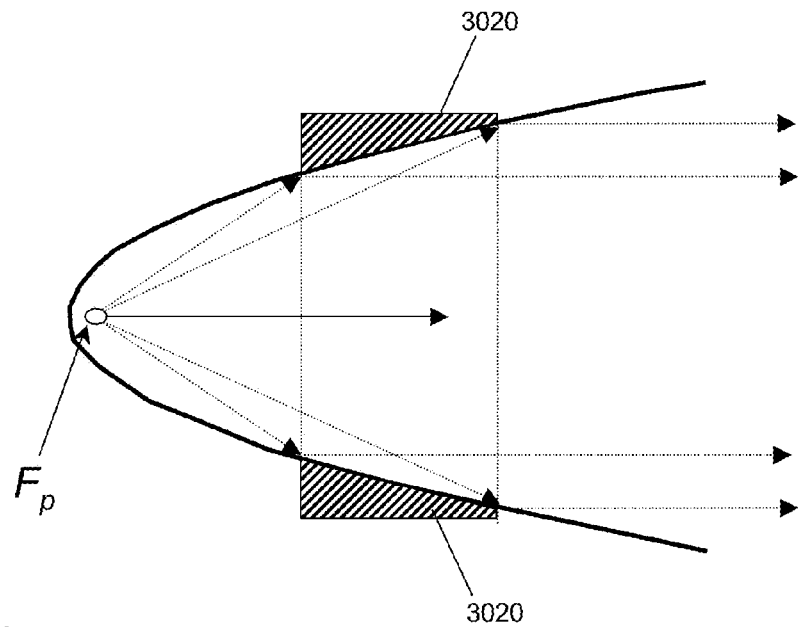
FIG. 11 illustrates a schematic cross-section of paraboloid optics.

This may be achieved by forming a spectroscopy system including both an x-ray source and a spectrometer, arranged in a confocal geometry to create a focused x-ray beam that excites the x-rays radiated from the object that are collected by the optical train FIG. 10 illustrates an example of a compact high brightness source being used to selectively illuminate a portion of an object 240 to be examined. In this illustration, the x-ray spectrometer system 3000 is the same as was illustrated in FIG. 4: an optical train 3100 comprising ellipsoidal optics 3010 collects x-rays from a point of focus 258 and forms an image onto an x-ray detection system 3200.

However, in this embodiment, the x-ray radiating region is not the large spot 248 as illustrated in FIG. 4, but is the tightly focused beam 255 from a compact high brightness x-ray source 2000, in combination with an optical train that comprises at least one x-ray optical element 2001 having the topology of an axially symmetric hollow tube comprising a quadric inner surface (in this example, an ellipsoidal surface). In some embodiments, this optical train may be a mirrored pair of paraboloidal optics while in others a mirrored pair of Wolter-type optics may be used.

The source 2000 comprises a vacuum chamber, in which electrons 111 bombard a specially constructed x-ray target comprising a substrate 1000 and several small discrete structures of x-ray generating material 1700 configured such that there is efficient heat transfer from the x-ray generating material to the substrate. This allows bombardment with higher currents and higher energy electrons, as the heat so generated may be effectively managed. This is partly achieved by using a substrate with high thermal conductivity, such as diamond.

The generated x-rays 888 pass through a window 1040 in the vacuum chamber and are collected by the ellipsoidal x-ray optical element 2001. On-axis and near-on-axis x-rays that are not collected by the optical element may be blocked using a beam stop 1850. The converging x-ray beam 889 from the x-ray source 2000 is positioned to focus onto the same position 258 in the object 240 where the optical train 3100 of the x-ray spectrometer system 3000 is aligned. By selectively illuminating only portions of the object 240 at a particular depth, the x-rays 2888-C collected by the x-ray spectrometer system 3000 are known to have originated from a particular lateral position (selected by the optics of the x-ray spectrometer system 3000) and a particular depth (selected by positioning the point of focus of the converging x-rays 889).

By adjusting the selected lateral and depth positions systematically, 3-D profiles of the object 240 may also be obtained.

Target designs and high brightness x-ray source configurations as may be used in embodiments of the present invention are described more fully in the following U.S. Patents and Patent Applications by the inventors and co-inventors of the present invention: STRUCTURED TARGETS FOR X-RAY GENERATION (U.S. patent application Ser. No. 14/465,816, filed Aug. 21, 2014), along with the provisional Applications incorporated therein and to which it claims benefit; X-RAY SOURCES USING LINEAR ACCUMULATION (U.S. Pat. No. 9,390,881, issued Jul. 12, 2016) along with the provisional Applications incorporated therein and to which it claims benefit; X-RAY SOURCES USING LINEAR ACCUMULATION (U.S. patent application Ser. No. 14/999,147 filed Apr. 1, 2016) along with the provisional Applications incorporated therein and to which it claims benefit; DIVERGING X-RAY SOURCES USING LINEAR ACCUMULATION (U.S. patent application Ser. No. 15/166,274 filed May 27, 2016), along with the provisional Applications incorporated therein and to which it claims benefit; all of which are hereby incorporated by reference in their entirety. Any of the x-ray source designs and configurations disclosed in the above referenced Patents and Patent Applications may be considered for use as a component in any or all of the methods or systems disclosed herein.

6. Variations in the Optical Train

As described in the examples above, the optical train for forming the x-ray image may comprise achromatic x-ray optical elements having the topology of a hollow tube, with an interior x-ray reflecting surface having a quadric profile. Quadric profiles include forms such as a spheroid, an ellipsoid, a paraboloid, a hyperboloid, an elliptic cylinder, a circular cylinder, an elliptic cone, and a circular cone.

The embodiment described above and illustrated in FIGS. 4-7, the quadric surface was an ellipsoidal surface having two foci, and the optical element is placed such that one of the foci is within the x-ray radiating region, and the other placed onto the detector, so that the x-rays radiated from the first focus are collected and converge to the second focus at the detector.

Another quadric surface that may be used is a paraboloid. Optical trains using optical elements having a paraboloidal surfaces were illustrated in the examples of FIGS. 8 and 9, and are shown in more detail in FIGS. 11-13B. The cross section of a paraboloid is a parabola that has a single focus point $F_p$ such that any photons radiated from the focus will be reflected emerge as a parallel (collimated) beam. By configuring the inner surface of a tube-shaped optical element 3020 to have a paraboloid surface, and choosing the coating for the reflecting portion of the tube such that the angle of incidence for the x-rays is smaller than the critical angle, total external reflection is achieved. Then, at least a portion of the x-rays generated by a source placed at the focus will emerge as a collimated beam of x-rays.

Figure 12:
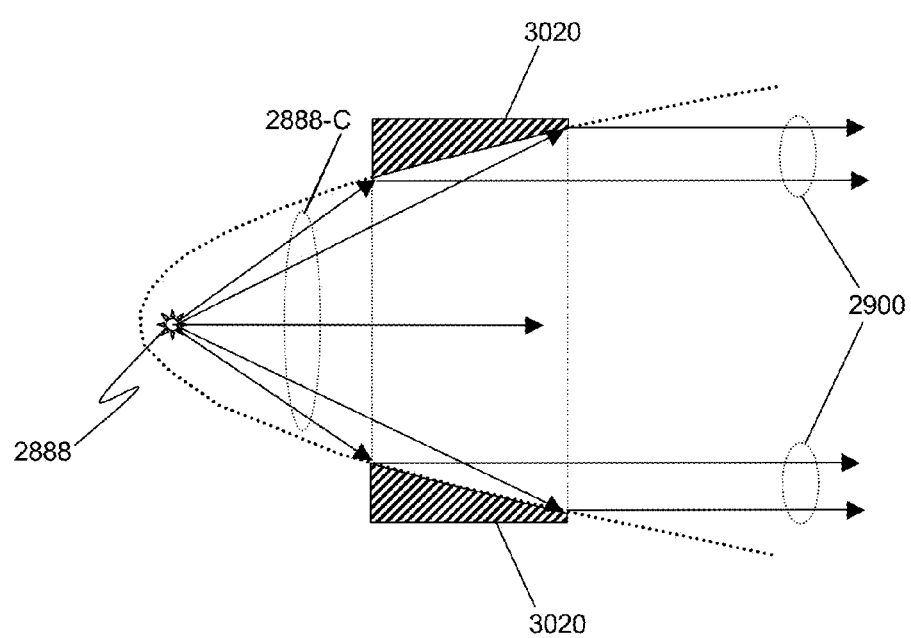
FIG. 12 illustrates a schematic cross-section schematic view of an optical train using a paraboloid optical element.

FIG. 12 illustrates a portion of an embodiment an optical train utilizing a paraboloidal reflector 3020. X-rays 2888 radiate from a point at the focus of the paraboloid, and a portion of the x-rays 2888-C enter the optical element 3020. A portion of the x-rays experience total external reflection from the inner paraboloidal surface of the tube-like optical element 3020, and become collimated x-rays 2900.

Figure 13A:
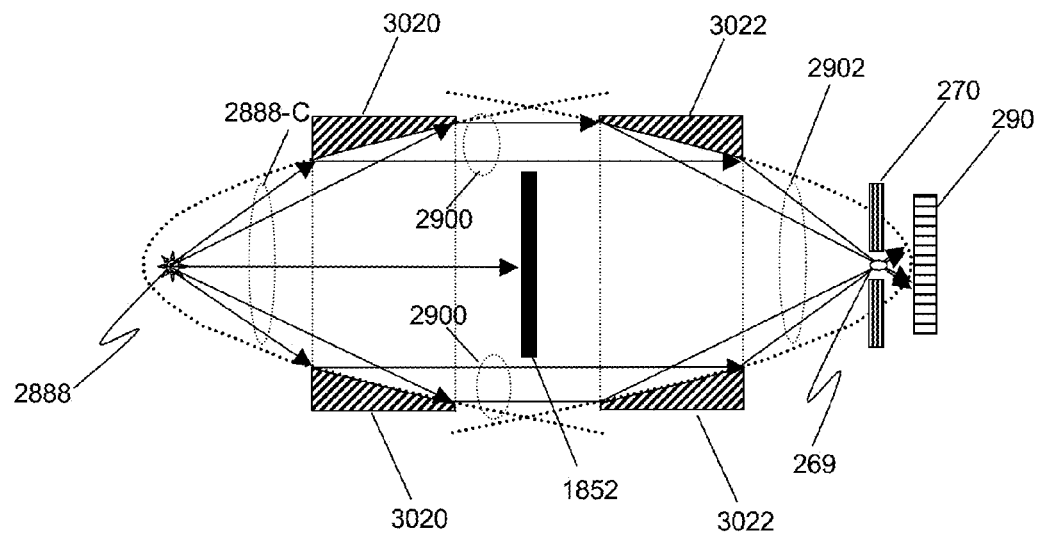
FIG. 13A illustrates a schematic cross-section schematic view of an optical train using a double paraboloidal optical element.
Figure 13B:
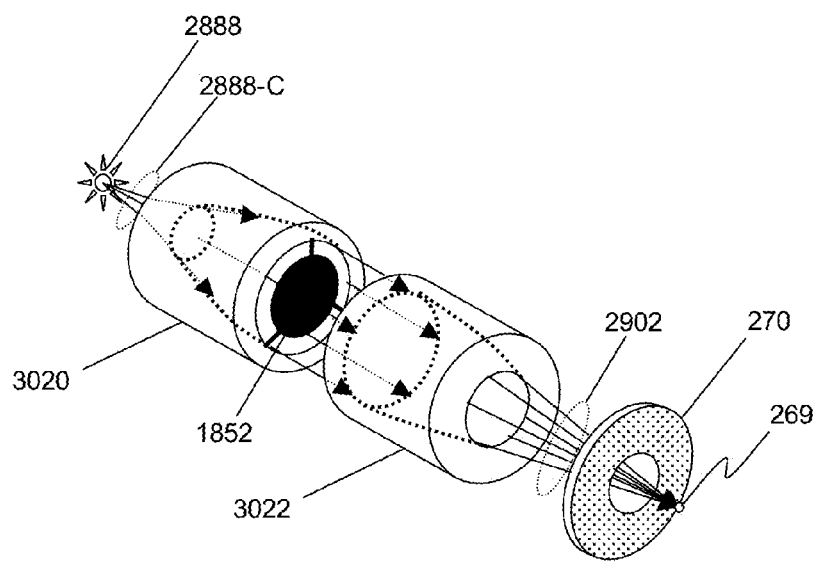
FIG. 13B illustrates a conceptual perspective view of the embodiment of the optical train shown in FIG. 13A.

Once collimated, a second optical element 3022 with a tube-shaped topology and paraboloidal inner surface, as shown in FIGS. 13A and 13B, may be aligned with the optical axis of the first optical element 3020 so that the collimated x-rays 2900 that are incident on the inner surface of the second optical element 3022 at angles smaller than the critical angle for the surface. The reflected x-rays form a bundle of converging x-rays 2902 that converge to a focus at the focus 269 of the second paraboloid. An aperture element 270 with the aperture overlapping the focus 269 and a detector 290 to detect x-rays that pass through the aperture provide elements of an x-ray detector for this embodiment.

Although the illustration shows a second paraboloidal optical element 3022 of the same size and shape as the initial paraboloidal optical element 3020, these need not be the same dimensions, but may have paraboloidal surfaces with different curvature and relative focus positions.

In some embodiments, as illustrated in FIG. 13A and the corresponding FIG. 13B, the on-axis x-rays may be blocked with a beam stop 1852.

Figure 14:
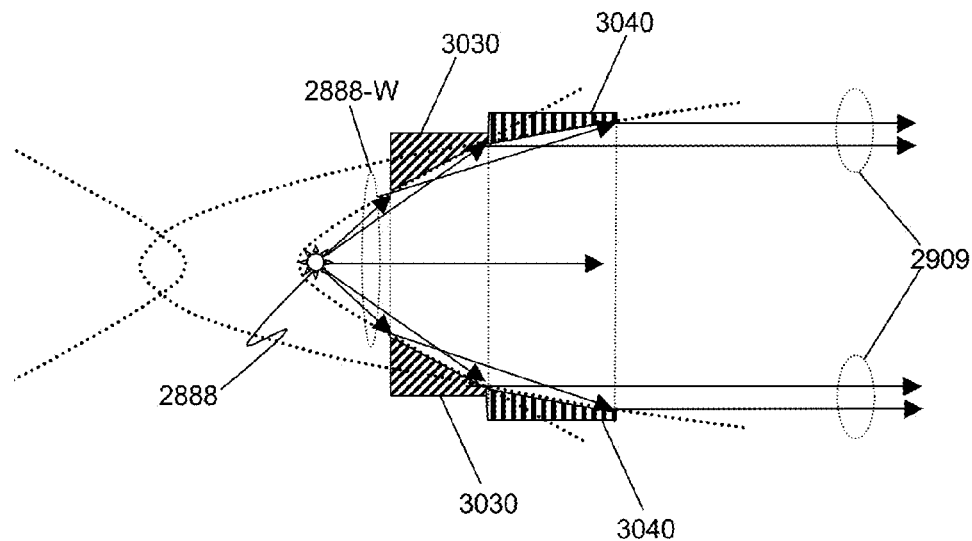
FIG. 14 illustrates a cross-section schematic view of an embodiment of an optical train using Wolter Type I optics.

FIG. 14 illustrates a portion of an embodiment an optical train utilizing a Wolter Type I optical design, in which one portion of the optic inner surface is ellipsoidal and one portion of the inner surface is hyperboloidal. X-rays 2888 radiate from a point at the focus of the paraboloid, and a portion of the x-rays 2888-W enter the optical element 3030. A portion of the x-rays experience total external reflection from the inner hyperboloidal surface of tube-like optical element 3030, and subsequently experience total external reflection from the inner elliptical surface of a tube-like optical element 3040, and become collimated x-rays 2909. These may then be used as in the other configurations for optical trains using collimated x-rays, in which a second set of optical elements focus the collimated beam. The focusing optic may comprise paraboloidal optical elements, as previously discussed, or may be Wolter Type I optics, in a mirror image of the collimating optics [see H. Wolter, Spiegelsysteme streifenden Einfalls als abbildende Optiken für Röntgenstrahlen, Annalen der Physik, vol. 10 (1952), pp. 94-114]. Such optical elements are further discussed in previously mentioned co-pending U.S. patent application Ser. No. 14/544,191, incorporated by reference in its entirety.

Figure 15:
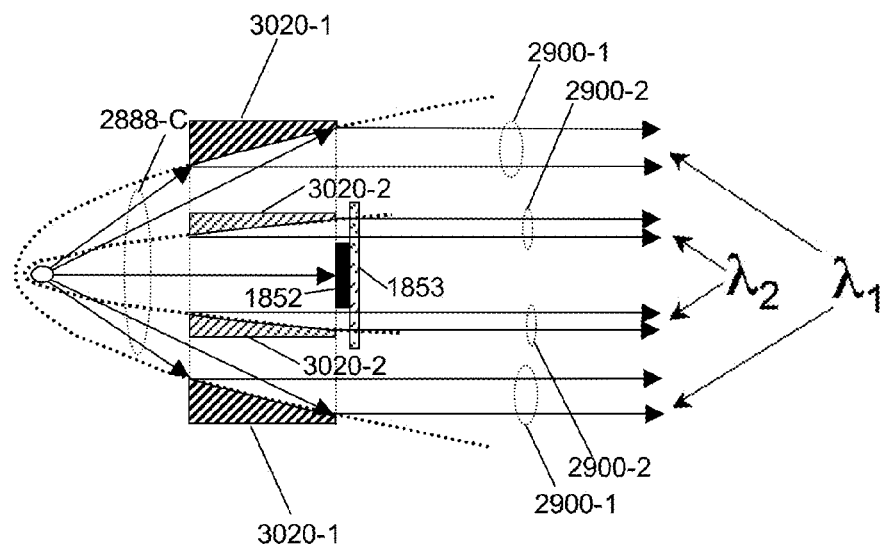
FIG. 15 illustrates a cross-section schematic view of a portion of a dual wavelength optical train using a set of nested paraboloid optical elements.

FIG. 15 illustrates the use of a nested set of co-axial optical elements aligned to provide two collimated beams of x-rays, each having different energies. As illustrated, the outer set of optics is a set of paraboloidal collimating optics 3020-1 designed collect x-rays at a larger angle, and will therefore provide total external reflection only for the lower energy x-rays (e.g. the Cu x-rays at 8.048 keV), producing a collimated beam of the lower energy x-rays 2900-1. The inner set of optics is also a set of paraboloidal collimating optics 3020-2 designed collect x-rays at a smaller angle, and will therefore provide total external reflection for both the low and high energy x-rays.

As in the previously described embodiments, a beam stop 1852 may be used to block the on-axis un-collimated x-rays. As shown in FIG. 15, however, this may be combined with a filter that 1853 that blocks the lower energy x-rays for the inner set of optics, allowing only the collimated beam of higher energy x-rays 2900-2 reflected from the second set of optics 3020-2 to be transmitted. This segregated spectral purity may be appropriate for many uses, depending on the downstream focusing optics that are used and the relative brightness of the different x-ray wavelengths generated.

The reflective coatings for the various x-ray optical elements used in embodiments of the invention as described above may be a single elemental material, to take advantage of the total external reflection for angles of incidence smaller than the critical angle, and preferably may be coated with a layer of higher mass density material (mass density greater than 2.5 g/cm$^3$) at least 25 nm thick. Or, the reflective coatings may be multilayer coatings, with alternating periodic layers of two or more materials, that provide constructive interference in reflection for certain wavelengths. The reflection efficiency depends on the wavelength and angle of incidence of the x-rays, and the thickness of the alternating layers, so this has limited use as a broadband reflector, but may be used if specific wavelengths are desired. Combinations that may be used for multilayer reflectors may be tungsten/carbon (W/C), tungsten/tungsten silicide (W/WSi$_2$), molybdenum/silicon (Mo/Si), nickel/carbon (Ni/C), chromium/scandium (Cr/Sc), and lanthanum/boron carbide (La/B$_4$C), and tantalum/silicon (Ta/Si), among others. The surface may also be a compound coating comprising an alloy or mixture of several materials. Individual optical elements may have one kind of coating, while other optical elements have other types of coatings. Quadric optical elements such as those disclosed herein can, with the appropriate surface and coating, have an x-ray throughput efficiency above 50%, and in some cases, greater than 60%.

7. Limitations and Extensions

With this application, several embodiments of the invention, including the best mode contemplated by the inventors, have been disclosed. It will be recognized that, while specific embodiments may be presented, elements discussed in detail only for some embodiments may also be applied to others. Also, details and various elements described as part of the prior art, or in the Applications incorporated by reference into the present Application, may also be applied to various embodiments of the invention.

While specific materials, designs, configurations and fabrication steps have been set forth to describe this invention and the preferred embodiments, such descriptions are not intended to be limiting. Modifications and changes may be apparent to those skilled in the art, and it is intended that this invention be limited only by the scope of the appended claims.

We claim:

1. An x-ray spectrometer system, comprising:
an x-ray imaging system having an object plane and an image plane, said x-ray imaging system comprising at least one achromatic x-ray optical element having an optical axis and an x-ray reflective surface, at least a portion of the x-ray reflective surface shaped in the form of a portion of a quadric surface, said x-ray imaging system positioned to collect fluorescence x-rays emitted from a portion of an object such that the object plane overlaps with a predetermined x-ray emitting volume and to form a fluorescence x-ray image of the collected fluorescence x-rays in the image plane; and
an x-ray detector system configured to detect x-rays of at least one predetermined spatially distinct sub-portion of the fluorescence x-ray image corresponding to a predetermined volume within the x-ray emitting volume of the object and to produce electronic signals that are related to the number of x-rays having specific energy values detected for said predetermined spatially distinct sub-portion of the fluorescence x-ray image, the x-ray detector system comprising at least one aperture configured to transmit x-rays corresponding to the predetermined spatially distinct sub-portion of the fluorescence x-ray image while attenuating other x-rays, the at least one aperture configured to be controllably moved relative to the at least one achromatic x-ray optical element.

2. The x-ray spectrometer system of claim 1, wherein the at least one aperture is positioned to be at the image plane.

3. The x-ray spectrometer system of claim 1, wherein the x-ray detector system comprises an x-ray detector element.

4. The x-ray spectrometer system of claim 3, wherein the x-ray detector element is selected from the group consisting of: a silicon drift detector, a Si(Li) detector, a Ge(Li) detector, and a PIN-diode.

5. The x-ray spectrometer system of claim 1, wherein the x-ray detector system comprises an energy resolving pixel array detector.

6. The x-ray spectrometer system of claim 1, wherein the x-ray imaging system has a point spread function with a full-width half maximum value greater than or equal to 0.1 micrometer and less than 20 micrometers.

7. The x-ray spectrometer system of claim 1, wherein the x-ray imaging system has a magnification greater than or equal to 1 and less than or equal to 20.

8. The x-ray spectrometer system of claim 1, in which the quadric surface is selected from the group consisting of: a spheroid, an ellipsoid, a paraboloid, a hyperboloid, an elliptic cylinder, a circular cylinder, an elliptic cone, and a circular cone.

9. The x-ray spectrometer system of claim 1, in which the quadric surface has a reflecting surface layer comprising a material selected from the group consisting of: boron carbide, silicon dioxide, silicon nitride, quartz, glass, chromium, copper, nickel, rhodium, palladium, gold, nickel, iridium, and platinum.

10. The x-ray spectrometer system of claim 1, in which the quadric surface has a reflecting surface comprising multilayers of pairs of materials, said pairs of materials selected from the group of material pairs consisting of: tungsten/carbon (W/C), tungsten/silicon (W/Si), tungsten/tungsten silicide (W/WSi$_2$), molybdenum/silicon (Mo/Si), nickel/carbon (Ni/C), chromium/scandium (Cr/Sc), lanthanum/boron carbide (La/B$_4$C), and tantalum/silicon (Ta/Si).

11. The x-ray spectrometer system of claim 6, in which the x-ray transmission efficiency for the x-ray imaging system is greater than 50%.

12. The x-ray spectrometer system of claim 1, wherein the x-ray detector system additionally comprises:
   at least one wavelength dispersive element to diffract the x-rays that have been transmitted through the at least one aperture; and
   an x-ray detector to detect the intensity of the diffracted x-rays.

13. The x-ray spectrometer system of claim 12, wherein the at least one wavelength dispersive element diffracts x-rays in different directions depending on their energy, and said x-ray detector is a position sensitive x-ray detector that detects the intensity of the x-rays diffracted at different directions by the at least one wavelength dispersive element.

14. The x-ray spectrometer system of claim 1, wherein the at least one aperture is configured to be controllably moved among different positions within the image plane of the at least one achromatic x-ray optical element.

15. The x-ray spectrometer system of claim 1, wherein the at least one aperture is configured to be controllably moved orthogonal to the optical axis of the at least one achromatic x-ray optical element.

16. The x-ray spectrometer system of claim 1, wherein the at least one aperture is configured to be controllably moved along the optical axis of the at least one achromatic x-ray optical element.

17. The x-ray spectrometer system of claim 1, wherein the at least one aperture is configured to be controllably moved relative to the at least one achromatic x-ray optical element for spatial mapping of different sub-volumes within the x-ray emitting volume.

18. The x-ray spectrometer system of claim 1, wherein the at least one achromatic x-ray optical element comprises an axially symmetric optic and the x-ray reflective surface comprises an inner surface of the axially symmetric optic.

19. An x-ray spectroscopy system, comprising:
   an x-ray source comprising:
      a vacuum chamber;
      a window transparent to x-rays attached to the wall of the vacuum chamber;
      at least one electron beam emitter within the vacuum chamber; and
      an anode target within the vacuum chamber, the anode target comprising:
         a substrate comprising a first selected material, and
         a planar first surface, from which thickness is measured in a direction perpendicular to the first planar surface, and two orthogonal lateral dimensions are measured parallel to the first planar surface; and
         a plurality of discrete structures embedded into the first planar surface of the substrate such that each of the plurality of discrete structures is in thermal contact with the substrate, the plurality of discrete structures comprising one or more materials selected for its x-ray generation properties in which at least two of the plurality of discrete structures are arranged on an axis parallel to the first planar surface of the substrate and passing through the first window, in which each of the discrete microstructures has a thickness of less than 20 microns, and a lateral dimension in the direction of the axis of less than 50 microns,
      the at least one electron beam emitter configured to direct electrons onto the at least two arranged discrete structures such that x-rays are generated from each of the at least two arranged discrete structures and at least a portion of the generated x-rays propagating on the axis from each of the at least two arranged discrete structures is transmitted through the window;
   a first optical train having an optical axis positioned to correspond to the axis on which the at least two discrete structures are arranged, the first optical train positioned to collect x-rays generated by the anode target and to produce an x-ray beam focused to a predefined position within an object;
   an x-ray imaging system having an object plane and an image plane, said x-ray imaging system comprising at least one achromatic x-ray optical element, said x-ray imaging system positioned to collect x-rays emitted from a portion of an object such that the object plane overlaps with a predetermined x-ray emitting volume and to form an image of the collected x-rays in the image plane; and
   an x-ray detector system configured to detect x-rays of at least one predetermined spatially distinct sub-portion of the x-ray image corresponding to a predetermined volume within the x-ray emitting volume of the object and to produce electronic signals that are related to the number of x-rays having specific energy values detected for said predetermined spatially distinct sub-portion of the x-ray image.

\* \* \* \* \*